US012305196B2

(12) United States Patent
Gross et al.

(10) Patent No.: US 12,305,196 B2
(45) Date of Patent: May 20, 2025

(54) COMPACT MECHANICAL SYRINGE EXTRUDER FOR 3D BIOPRINTING OF CELL LADEN GELS

(71) Applicant: CEDARS-SINAI MEDICAL CENTER, Los Angeles, CA (US)

(72) Inventors: Andrew R. Gross, Los Angeles, CA (US); Dhruv Sareen, Porter Ranch, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 1024 days.

(21) Appl. No.: 17/254,783

(22) PCT Filed: Jun. 26, 2019

(86) PCT No.: PCT/US2019/039277
§ 371 (c)(1),
(2) Date: Dec. 21, 2020

(87) PCT Pub. No.: WO2020/006096
PCT Pub. Date: Jan. 2, 2020

(65) Prior Publication Data
US 2021/0269776 A1 Sep. 2, 2021

Related U.S. Application Data

(60) Provisional application No. 62/691,492, filed on Jun. 28, 2018.

(51) Int. Cl.
C12M 1/00 (2006.01)
B33Y 30/00 (2015.01)
(Continued)

(52) U.S. Cl.
CPC ............ *C12N 5/0691* (2013.01); *B33Y 30/00* (2014.12); *B33Y 70/00* (2014.12); *C12N 5/0696* (2013.01);
(Continued)

(58) Field of Classification Search
None
See application file for complete search history.

(56) References Cited

U.S. PATENT DOCUMENTS 2,498,672 A    2/1950   Glass
6,645,177 B1*  11/2003  Shearn ................ A61M 5/1456
                                                         604/67
(Continued)

FOREIGN PATENT DOCUMENTS

WO   WO2017/040975 A1 *  3/2017
WO      2018089515 A1    5/2018
WO      2020006096 A1    1/2020

OTHER PUBLICATIONS

International Search Report and Written Opinion for PCT/US2019/39277 dated Sep. 18, 2019, 8 pages.
(Continued)

Primary Examiner — Jyoti Nagpaul
(74) Attorney, Agent, or Firm — Nixon Peabody LLP

(57) ABSTRACT

Bioprinting is the layer-by-layer construction of synthetic tissues or scaffolds. Described herein is a motorized extruder which can precisely extrude and retract extrudate such as bioinks in a compact and rapidly-loadable form-factor. This includes a compact bioprinter using a stepper motor coupled with a threaded shaft to directly move the plunger of an extruder. This pneumatic-mechanical system obviates the needs for pneumatic tubing, rods, or other complex elements of existing designs. The direct drive design further allows for a lighter, smaller gantry that is capable of more precise
(Continued)

fabrication of bioprinted constructions. This includes delicate vasculature systems that are beyond limits of existing bioprinting technologies.

18 Claims, 12 Drawing Sheets

(51) Int. Cl.
*B33Y 70/00* (2020.01)
*C12N 5/071* (2010.01)
*C12N 5/074* (2010.01)
*B33Y 50/02* (2015.01)

(52) U.S. Cl.
CPC ........... *B33Y 50/02* (2014.12); *C12N 2533/52* (2013.01); *C12N 2533/54* (2013.01)

(56) References Cited

U.S. PATENT DOCUMENTS

2016/0068385 A1* 3/2016 Chen ................ B81C 1/00119
422/503
2017/0369827 A1 12/2017 Langenfeld et al.

OTHER PUBLICATIONS

Leberfinger et al., Concise Review: Bioprinting of Stem Cells for Transplantable Tissue Fabrication, Stem Cells Translational Medicine, 2017, pp. 1940-1948.

Mirabella et al., 3D-Printed Vascular Networks Direct Therapeutic Angiogenesis in Ischaemia, Nat Biomed Eng., 2017, 1-20.

Zhu et al., Direct 3D bioprinting of prevascularized tissue constructs with complex microarchitecture, Biomaterials, 2017, pp. 1-21.

* cited by examiner

FIG. 3A
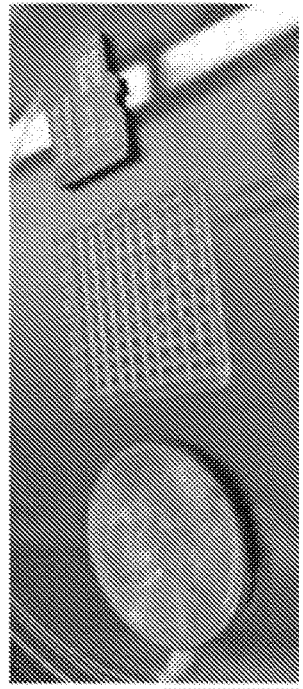
FIG. 3D
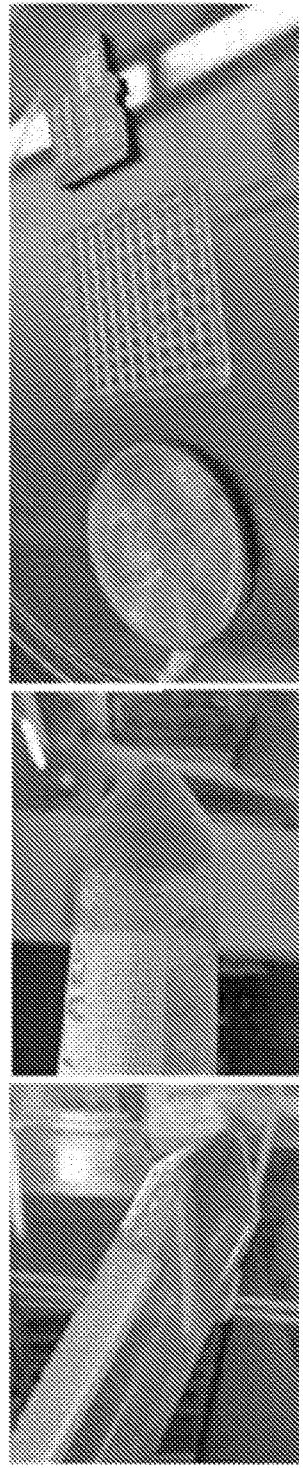
FIG. 3C
FIG. 3B

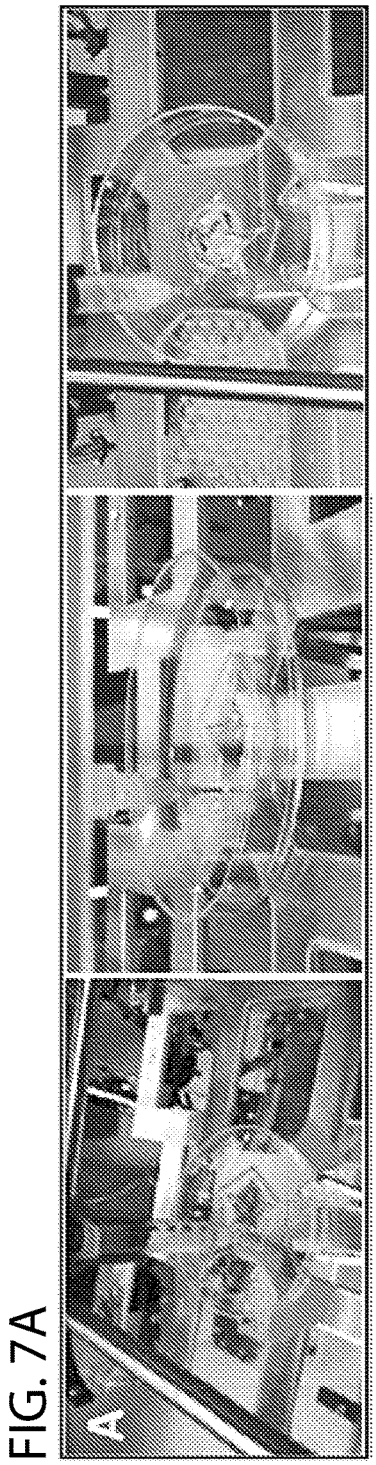
FIG. 7A
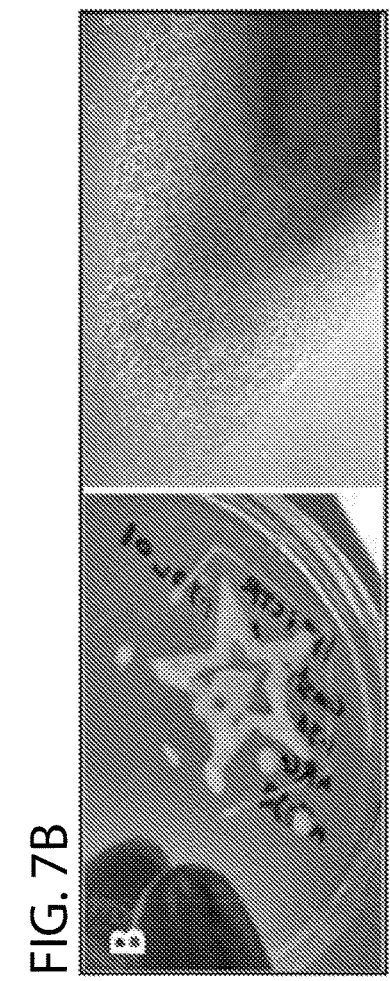
FIG. 7B
FIG. 7C
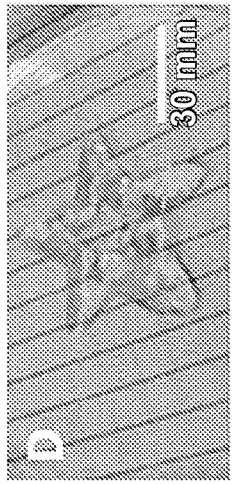
FIG. 7D
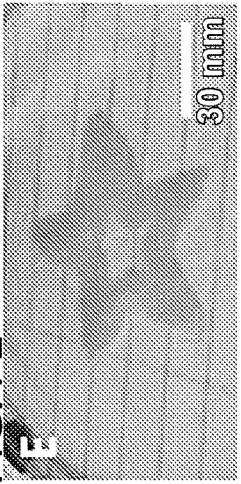
FIG. 7E
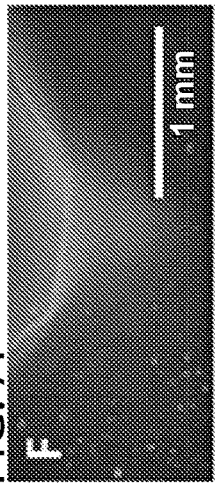
FIG. 7F
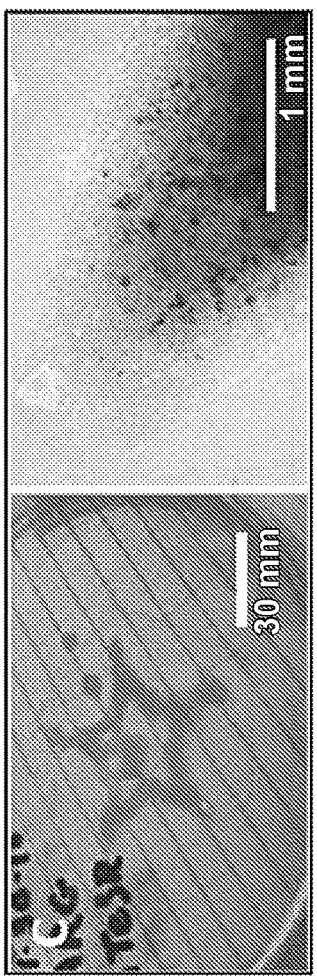

| Model | Step distance mm/step | Motor Length L(mm) | Rate Voltage (V) | Rate Current (A) | Phase Resistance (Ω) | Phase Inductance (mH) | Holding Torque (N.m) | Lead Wire (NO.) | Detent Torque (kg.cm) | Rotor Inertia (kg.cm$^2$) | Motor Weight (kg) |
|---|---|---|---|---|---|---|---|---|---|---|---|
| 39BYGL215A | 0.01 | 34 | 12 | 0.4 | 30 | 42 | 0.21 | 4 | 0.12 | 0.02 | 0.18 |

COMPACT MECHANICAL SYRINGE EXTRUDER FOR 3D BIOPRINTING OF CELL LADEN GELS

CROSS-REFERENCE TO RELATED APPLICATIONS

This application is a National Phase of International Application No. PCT/US2019/039277, filed Jun. 26, 2019, which designated the U.S. and that International Application was published under PCT Article 21(2) in English, which claims priority under 35 U.S.C. § 119(e) to U.S. provisional patent application No. 62/691,492 filed Jun. 28, 2018, the entirety of each of which are hereby incorporated by reference.

FIELD OF THE INVENTION

The described technology relates to a bioprinter system for fabricating systems including depositing cells in an organized fashion for analysis.

BACKGROUND

Bioprinting is the layer-by-layer construction of synthetic tissues or scaffolds in order to generate tissues with greater similarity to natural tissues for modeling organs (for research, such as drug discovery) and medicine (such as transplantation). While bioprinters exist on the market, including pneumatic and mechanical systems, they are significantly limited in precision and simplicity when exerting force to extrude materials on a surface, including bioinks with cells in a substrate. For example, pneumatic vacuum pressure through tubing may leak or transit through long pneumatic tubing is damaging to cells in bioink. Mechanical systems are bulky and need a large rod; a gantry surrounding the extruder is moved along the rod to exert pressure. There is a great need in the art for a system that achieves a series of criteria, including precision, retraction, compact size, rapid loading, and low cost.

Described herein is a motorized extruder which can precisely extrude and retract extrudate such as bioinks in a compact and rapidly-loadable form-factor. This includes a compact bioprinter using a stepper motor coupled with a threaded shaft to directly move the plunger of an extruder (e.g., syringe). This pneumatic-mechanical system obviates the needs for pneumatic tubing, rods, or other complex elements of existing designs. The direct drive design further allows for a lighter, smaller gantry that is capable of more precise fabrication of bioprinted constructions. This includes delicate vasculature systems that are beyond limits of existing bioprinting technologies.

SUMMARY OF THE INVENTION

Described herein is a bioprinter for dispensing at least one biomaterial, comprising s processor configured to determine a path; a support assembly, comprising one or more linear rods; a gantry comprising: at least one extruder, each extruder comprising a nozzle and a tube, a plunger, a threaded shaft, a stepper motor, wherein the processor is operatively coupled to the support assembly to move the one or more linear rods along a determined path, and operatively coupled to the stepper motor, wherein the one or more linear rods are attached to the gantry, wherein the plunger is inside the tube and comprises a means for attachment to the threaded shaft, wherein the threaded shaft is mechanically coupled to the stepper motor, wherein the nozzle is at one end of the tube. In other embodiments, the means for attachment to the threaded comprises reciprocating members on each of the plunger and threaded shaft. In other embodiments, the reciprocating members are a snap fit coupling. In other embodiments, the bioprinter comprises two extruders. In other embodiments, the plunger is configured to exert pressure through the nozzle. Also described herein is a bioprinted assembly made by the bioprinter. In other embodiments, the bioprinted assembly includes vascular cells in an organized fashion deposited on a substrate. In other embodiments, the bioprinted assembly includes one or more non-vascular cells. In other embodiments, the non-vascular cells are derived from induced pluripotent stein cells (iPSCs).

Also described herein is a bioprinted assembly, comprising a layer of vascular cells in an organized fashion deposited on a substrate n other embodiments, the bioprinted assembly includes induced pluripotent stem cell endothelial cells (iECs). In other embodiments, the bioprinted assembly includes one or more non-vascular cells. In other embodiments, the bioprinted assembly includes non-vascular cells are derived from induced pluripotent stem cells (iPSCs).

Also described herein is a bioink, including a quantity of at least one cell type suspended in a substrate suitable for bioprinting. In other embodiments, the bioink includes induced pluripotent stem cell endothelial cells (iECs). In other embodiments, the bioink includes one or more non-vascular cells. In other embodiments, the non-vascular cells are derived from induced pluripotent stem cells (iPSCs). In other embodiments, the substrate comprises one or more of cell culture media, gelatin and fibrinogen.

BRIEF DESCRIPTION OF THE FIGURES

FIG. 3. Bioinks containing induced pluripotent stem cells. Bioinks as shown in 6-well place (A), Bioink containing cell culture medium, gelatin, and fibrinogen (B). At 37° C., this ink can be pipetted to suspend cells and fill a syringe (C). At room temperature it gels, allowing it to be built upon (D). Silicone can be printed to form scaffolds and microfluidic devices.

FIG. 7. Exemplary results. The printer and ink achieved excellent detail, which has continued to improve as settings are optimized (A). An initial printed construct two days after printing (B) and 6 days after printing (C) retained shape. A taller print immediately after printing (D) and after three days (E) also showed excellent cell survival. Printed nuclear GFP stem cells under fluorescence, 3 days post printing (F) were visible inside of the 3 mm tall structure.

DETAILED DESCRIPTION

Figure 1A:
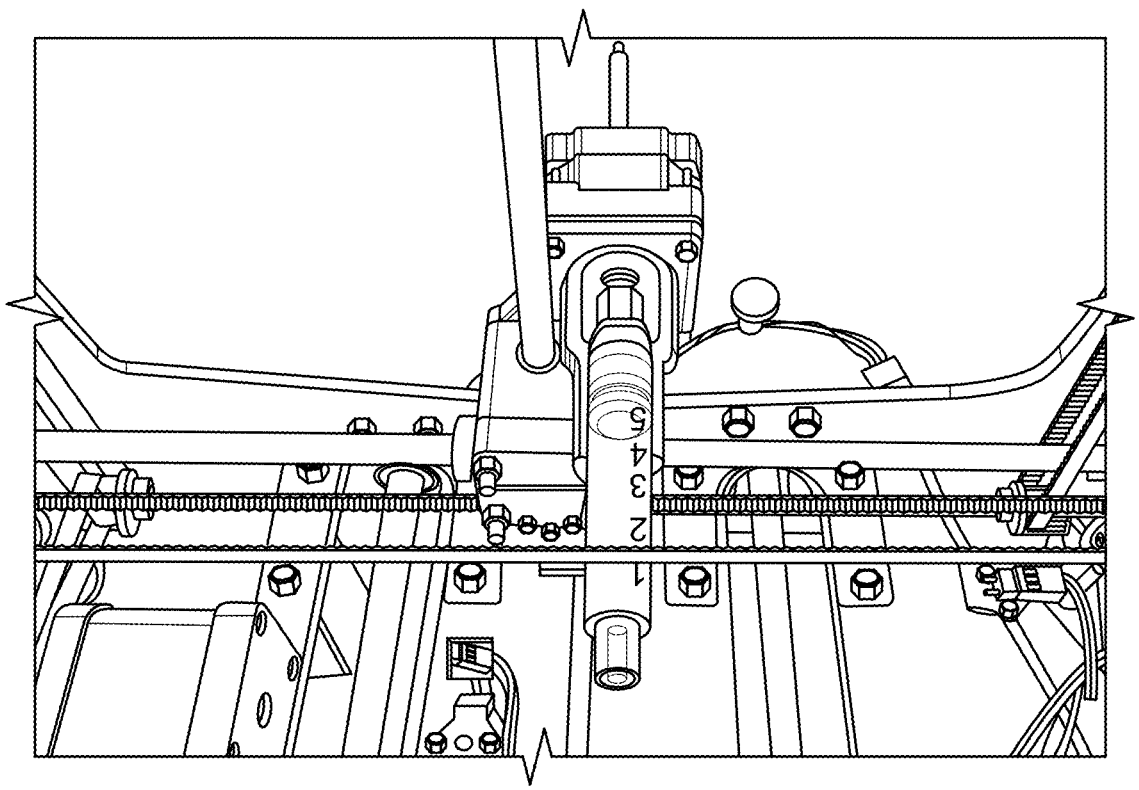
FIG. 1. Various perspectives of an embodiment. As shown, the bioprinter includes a motorized extruder (A) that obviated the needs for a bulky linear rail system (B). Instead of coupling a threaded shaft to a fixed shaft on a stepper motor, the stepper motor turns a threaded shaft directly. The syringe snaps into place (C), and the plunger itself couples to the shaft with a snap-fit coupling (D).
Figure 1B:
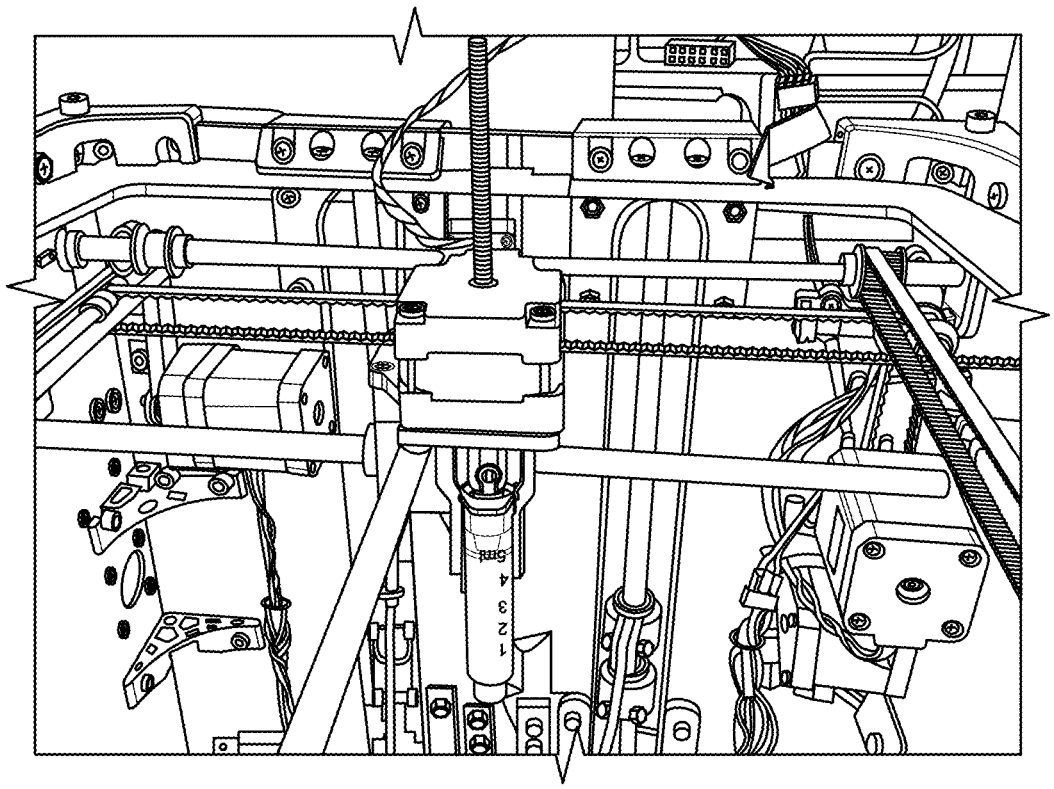
Figure 1C:
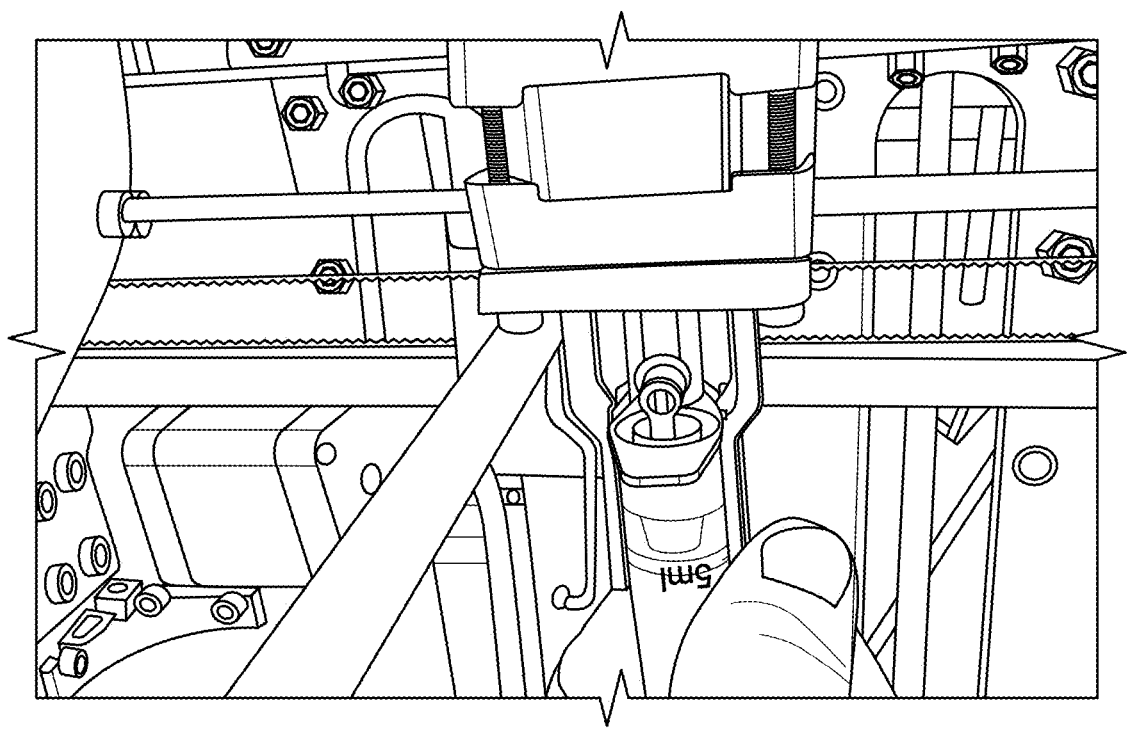
Figure 1D:
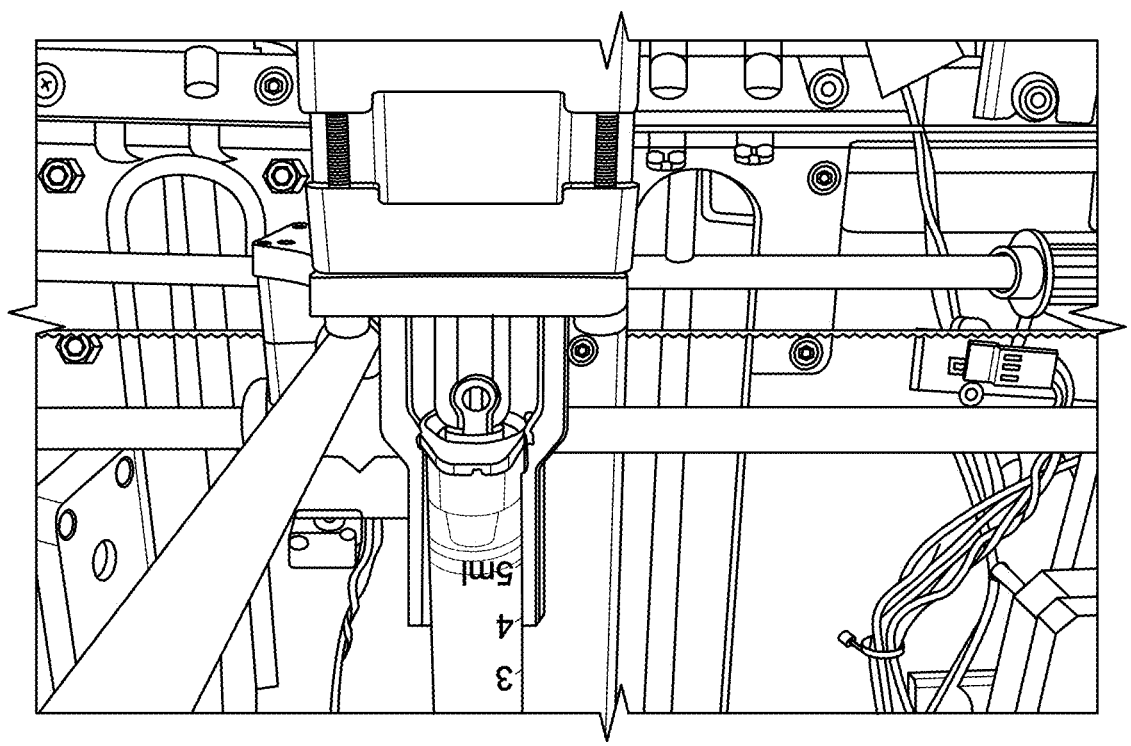

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., Revised, J. Wiley & Sons (New York, NY 2006); and Sambrook and Russel, *Molecular Cloning: A Laboratory Manual* $4^{th}$ ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. 3D bioprinting allows researchers to construct synthetic tissues that replicate the structure and environment of living mammalian tissues far better than planar cells on a plastic dish can. Cells of many kinds can be deliberately arranged to study cell-cell interactions, and can also be vascularized to model cellular interactions in a manner not otherwise accounted for in traditional cell culture formats. This has the potential to create models which recapitulate natural functions: blood brain barrier models for drug permeability studies; kidneys with functional nephrons; bulk liver tissues with ducts; synthetic pancreas with working islets.

In addition to depositing various cell types, 3D bioprinting can also be used to build soft, biocompatible structures for study biophysical and biomechanical effects. For example, permeable scaffolds can be printed to study osteoclast migration. Soft domes can be made to support corneas in culture.

As bioprinting advances, its use is likely to be adopted throughout biomedical research to replace materials and methods which are currently employed simply due to a lack of available alternatives. Importantly, existing techniques are in capable of precise deposition of cells in a manner nearing relevant physiological distances. Specifically, precision deposition of stem cells requires that the printhead be as small and light as possible in order to reduce the inertia the gantry must contend with. Traditional designs are too bulky to approximate vasculature on printed surfaces, with such physiological features being an important feature to incorporated if one is to faithfully model living systems.

While achieving a small size can be done by relying on a pneumatic system (since this offloads the mechanics from the gantry completely), but doing so is extremely expensive and one must contend with issues related to stable sealing for pressure generation and maintenance, along with pneumatic tubing transit that is damaging to cell viability. Only top-tier machines can achieve retraction, which is vital to prevent leakage.

Mechanical systems offer precision, retraction, and can be made rapidly-loadable. But the size is prohibitive, since available options drive a plunger along rails, which requires the entire length of the plunger to be available between the motor and the back end of the syringe. Gantry sizes also tend to be larger in such systems.

Described herein is a motorized extruder that overcomes size limitations by removing the bulky linear rail system. Instead of coupling a threaded shaft to a fixed shaft on a stepper motor, the stepper motor turns a threaded shaft directly. The syringe snaps into place, and the plunger itself couples to the shaft with a snap-fit coupling. Manual plunging of the syringe for loading and unloading is achieved with a plunger extension that couples to the miniaturized plunger using the same snap coupling as the motor.

A key advantage for a mechanical drive over pneumatic is that the pneumatic response varies with ink viscosity, and will undesirably eject completely if the pressure is set slightly too high. Pneumatic systems also require additional hardware to back-drive in order to retract extrudate, which is a common and important feature in conventional FDM printing that mechanical extruders perform without challenge.

As a renewable and flexible source of cellular materials for printing, Induced Pluripotent Stem Cells (iPSCs) ideal for bioinks. Nevertheless, iPSCs are highly sensitive to their environment. In order to prevent contamination and limit the time spent during printing, it is necessary to be able to load bioinks as quickly as possible and with minimal exposure to possible sources of contamination. Meeting these needs while keeping the size of a print head low enough to print successfully in a sterile environment requires a system with precision, retraction, compact size, rapid loading, and low cost.

Figure 11:
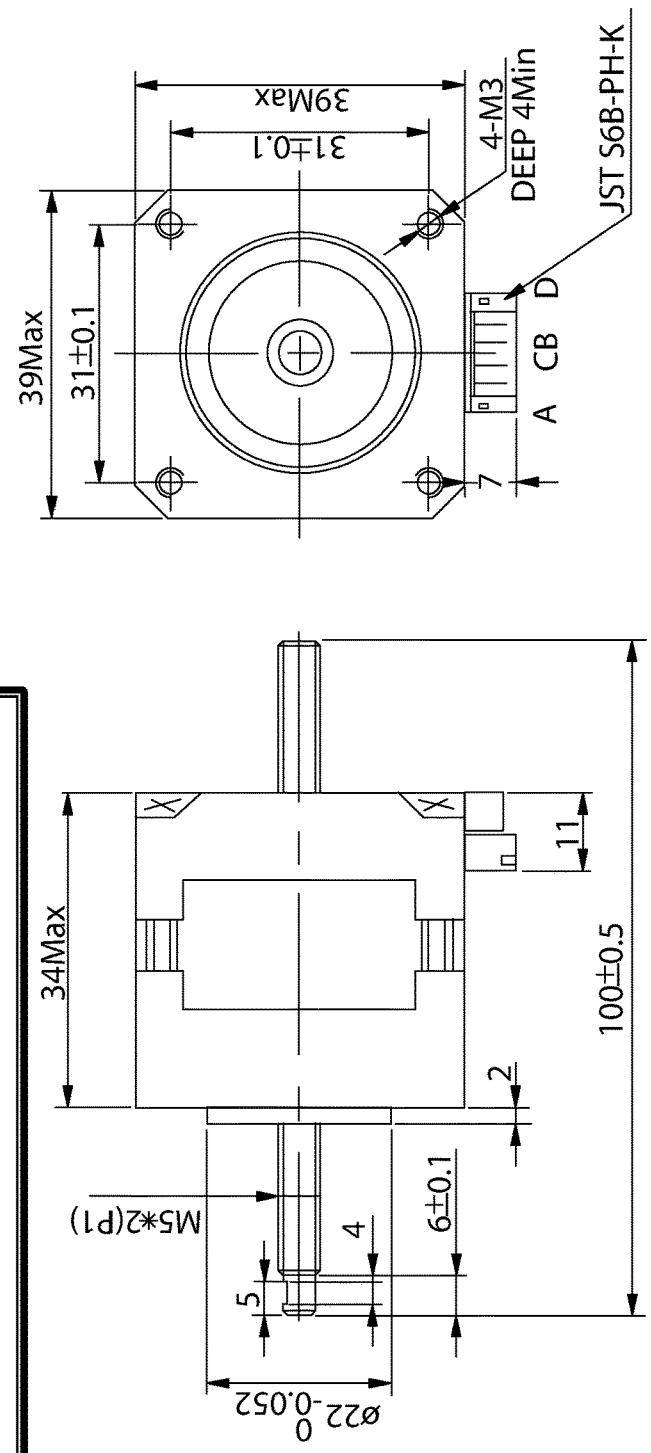
FIG. 11. Stepper motor compatible with the bioprinter.

Described herein is a bioprinter for dispensing at least one biomaterial, comprising s processor configured to determine a path; a support assembly, comprising one or more linear rods; a gantry comprising: at least one extruder, each extruder comprising a nozzle and a tube, a plunger, a threaded shaft, a stepper motor, wherein the processor is operatively coupled to the support assembly to move the one or more linear rods along a determined path, and operatively coupled to the stepper motor, wherein the one or more linear rods are attached to the gantry, wherein the plunger is inside the tube and comprises a means for attachment to the threaded shaft, wherein the threaded shaft is mechanically coupled to the stepper motor, wherein the nozzle is at one end of the tube. In various embodiments, the tube and plunger are configured to exert pressure through the nozzle. For example, extruding a bioink through the nozzle at the end of the tube. In various embodiments, the processor operatively coupled to the stepper motor mechanically attached to the threaded shaft with a means for attachment to the plunger in the tube, thereby controls exerted pressure through the nozzle of the tube. In other embodiments, the means for attachment to the threaded comprises reciprocating members on each of the plunger and threaded shaft. In other embodiments, the reciprocating members are a snap fit coupling. In other embodiments, the bioprinter comprises two extruders. In other embodiments, the plunger is configured to exert pressure through the nozzle. As an example, a compatible stepper motor includes a hybrid linecar actuator motor such as MPN ROB-10848 as depicted in FIG. 11. In various embodiments, the threateded shaft is about 5, 6, 7, 8, 9, 10, 11, 12, 13, 14, or 15 cm long with a shaft traveling 0.001-0.005, 0.005-0.01, 0.01-0.02 mm/step, about 50-100, 100-200 steps per revolution. For example, the threaded shaft is 10 cm long with an M5 P1 shaft that travels 0.01 mm/step, 200 steps per revolution, in various embodiments, compatible syringes range from 3 mL to 10 mL.

Also described herein is a method of using the bioprinted, including the process outlined in Example 1.

Also described herein is a bioprinted assembly made by the bioprinter. In other embodiments, the bioprinted assembly includes vascular cells in an organized fashion deposited on a substrate. In other embodiments, the bioprinted assembly includes one or more non-vascular cells. In other embodiments, the non-vascular cells are derived from induced pluripotent stem cells (iPSCs). In various embodiments, the bioprinted assembly includes a bioink. Examples of compositions of bioinks include Fibrinogen-Gelatin (F-G) Bioink, Fibrinogen-Gelatin-Thrombin (F-G-T) Bioink, and Pluronic F-127 as listed in Tables 11, 12, and 13. This includes constructs according to the process and designs outlined in Example 1.

Also described herein is a bioprinted assembly, comprising a layer of vascular cells in an organized fashion deposited on a substrate. In other embodiments, the bioprinted assembly includes induced pluripotent stem cell endothelial cells (iECs). In other embodiments, the bioprinted assembly includes induced pluripotent stem cell brain microvascular endothelial cells (iBMECs). In other embodiments, the bioprinted assembly includes one or more non-vascular cells. In other embodiments, the bioprinted assembly includes ion-vascular cells are derived from induced pluripotent stem cells (iPSCs). As one example, this include induced motor neurons (iMNs), pancreatic cells, or skin fibroblasts. In other embodiments, the organized fashion includes a vascular network defining at least one central channel, wherein the vascular network is positioned in a selected pattern to define void space. In various embodiments, the non-vascular cells are within the void space in another embodiment, vascular network is configured to permit diffusion of a liquid, such as cell culture media, from the at least one central channel to non-vascular cells. In other embodiments, the substrate includes one or more pre-printed constructs in an organized fashion. In various embodiments, the pre-printed constructs include a bioink Examples of compositions of bioinks include Fibrinogen-Gelatin (F-G) Bioink, Fibrinogen-Gelatin-Thrombin (F-G-T) Bioink, and Pluronic F-127 as listed in Tables 11, 12, and 13. In various embodiments, the pre-printed constructs include polymers, such as thermosensitive or light sensitive polymers, gel matrices, or other biocompatible materials readily known to one of skill in the art. In various embodiments, the one of more vascular cells are in a construct of larger than 100-200, 200-400, 400 or more µm. In various embodiments, the vascular network defining at least one channel includes channels of less than 100-200 µm. Also described herein is a bioink, including a quantity of at least one cell type suspended in a substrate suitable for bioprinting. In other embodiments, the bioprinted assembly includes induced pluripotent stem cell endothelial cells (iECs). In other embodiments, the bioink includes induced pluripotent stem cell brain microvascular endothelial cells (iBMECs). In other embodiments, the bioink includes one or more non-vascular cells. In other embodiments, the non-vascular cells are derived from induced pluripotent stem cells (iPSCs). As one example, this include induced motor neurons (iMNs), pancreatic cells, or skin fibroblasts.

In another example, iECs can be made by culturing (iPSCs) in the presence of CHIR99012 for about 2 days to generate mesoderm, culturing mesoderm in the presence of BMP4, VEGF, and FGF2 for about 2 days to generate vascular progenitor cells, culturing vascular progenitors in the presence of EGM-MV2 and VEGF for about 4-6 days to generate endothelial progenitor cells, and culturing endothelial progenitor cells in the presence of EGM-MV2 and VEGF to generate endothelial cells. In various embodiments, the vascular progenitors are cultured in the presence of EGM-MV3 and VEGF, and passages 2, 3, 4 or more times to generate endothelial cells. For example iECs can express key markers such as CD31, CD34, VEGF, and VEGFA. Using a combination of growth factors, the Inventors were able to successfully produce endothelial cell types. Based on the described protocols, it appears that endothelial markers are more and purely expressed in Day 20 compared to Day 10 of differentiation→time for maturation. Differentiation to be confirmed with other experiments: Dil-ac-LDL uptake, and TEER (resistance). Further information is found in PCT App. No. US2019/23749, which is fully incorporated by reference herein.

In other embodiments, the substrate comprises matrix components or hydrogels. In various embodiments, hydrogels include natural hydrogels such as collagen, fibrin, chitosan, and alginate and synthetic hydrogels such as gelatin, Pluronic, and polyethylene glycol. In other embodiments, the substrate comprises a thermosensitive or light sensitive polymer. In other embodiments, the substrate comprises one or more of cell culture media, gelatin and fibrinogen. Examples of compositions of bioinks include Fibrinogen-Gelatin (F-G) Bioink, Fibrinogen-Gelatin-Thrombin (F-G-T) Bioink, and Pluronic F-127 as listed in Tables 11, 12, and 13.

Example 1

Bioprinting may enable researchers to overcome limitations of current methods to construct macro-scale structures, organize different cell types together, and generate very specific shapes. To overcome size limitations, bioprinting is accomplished by generating a 3D computer model; generating a series of cross-sections of the model; then instructing a printhead to draw each cross-section and deposit material to construct the original 3D shape layer-by-layer.

Example 2

Bioprinter Incorporating Stepper Motor and Threaded Shaft

Figure 2A:
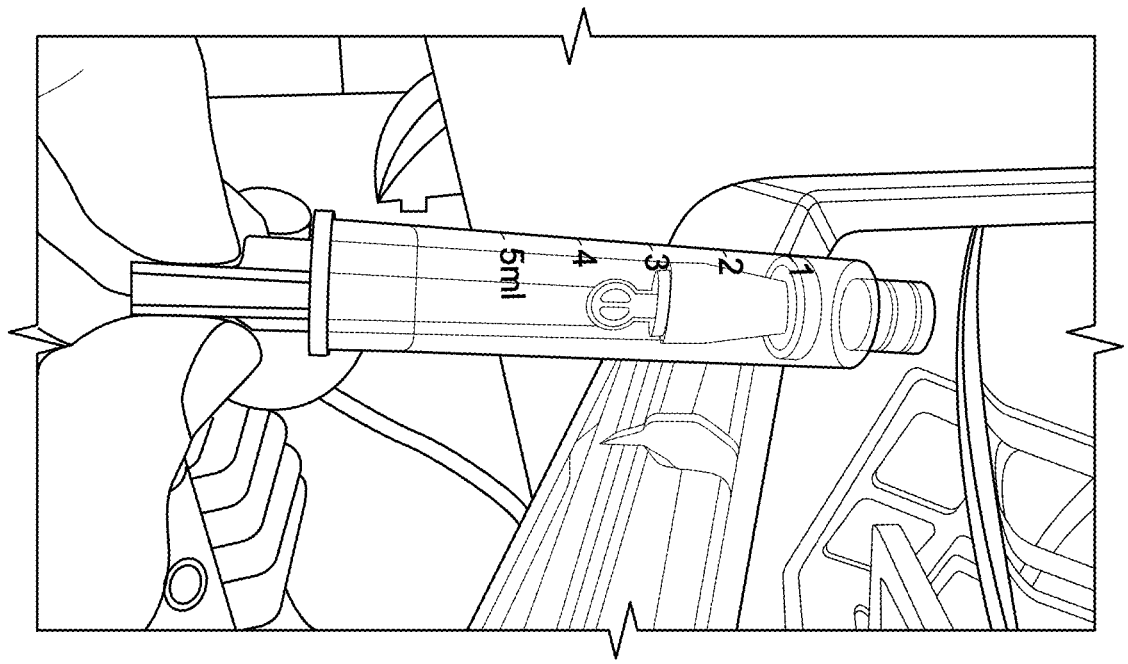
FIG. 2. Manual plunger extension. Manual plunging of the syringe for loading and unloading (A) is achieved with a plunger extension that couples to the miniaturized plunger using the same snap coupling (B) as the motor.
Figure 2B:
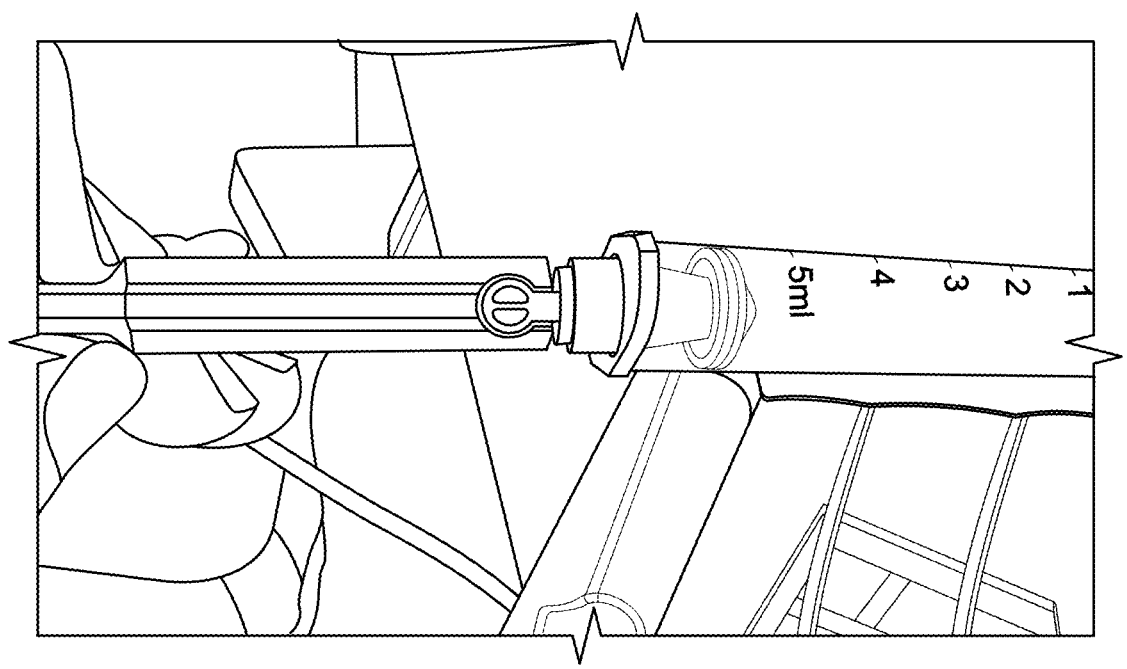
Figure 5A:
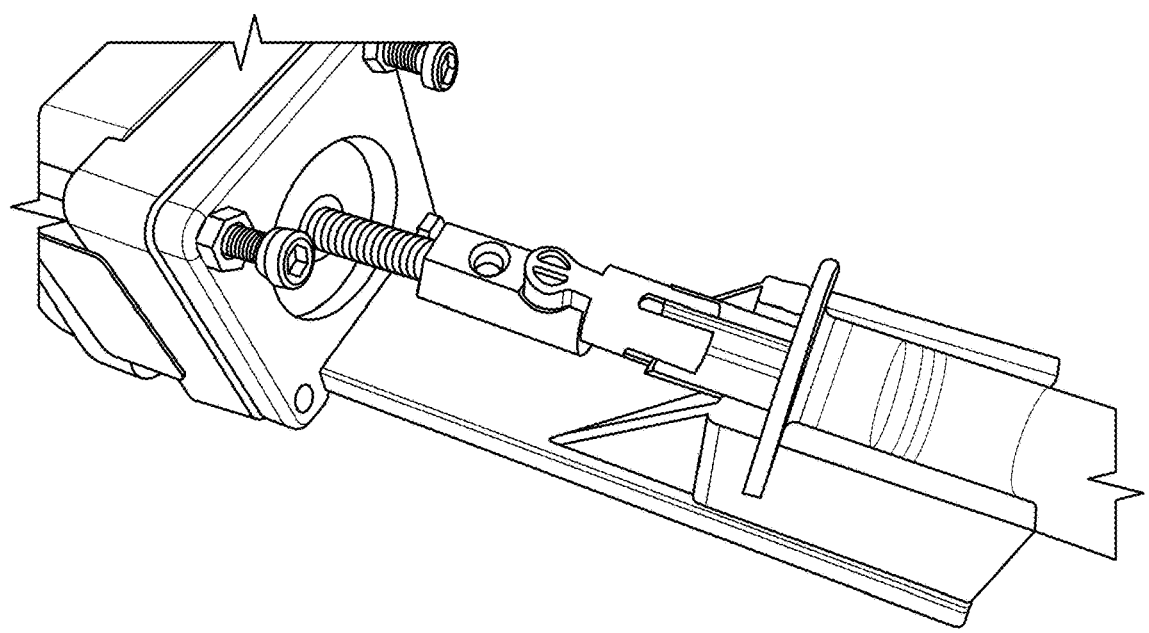
FIG. 5. Another depiction of assembly together. Another depiction of the assembly showing the stepper motor, threaded shaft, with snap-fit coupling to syringe (A). Another depiction stepper motor, threaded shaft and syringe, as controlled by circuit board (B).
Figure 5B:
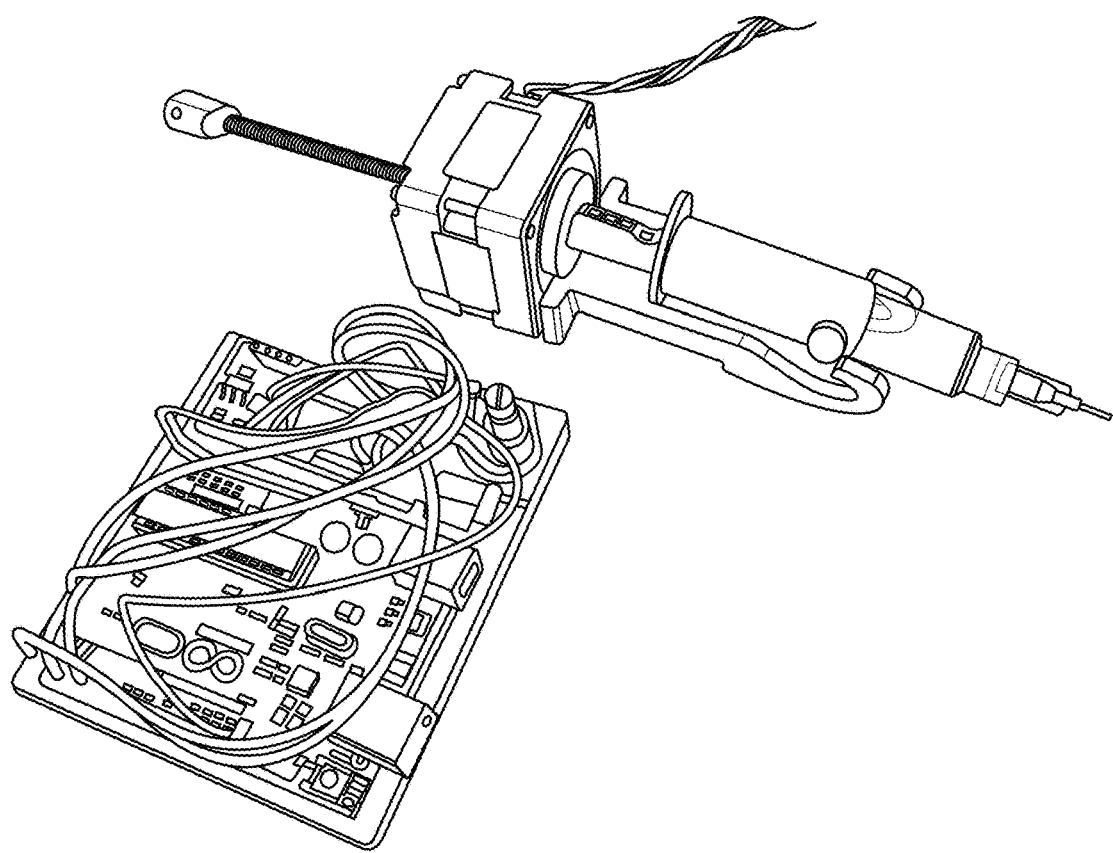

As shown in FIG. 1, the bioprinter includes a motorized extruder that obviates the needs for a bulky linear rail system. Whereas conventional designs couple a threaded shaft to a fixed shaft on a stepper motor, the stepper motor turns a threaded shaft directly. This obviates the need for pneumatic vacuum pressure systems and also reduces the gantry size, which allows for higher precision printing due to decreased weight removal of components that otherwise reduce tolerances due to mechanical play. The threaded shaft snaps into place for a plunger on a syringe, eliminating another source of mechanical play, by using a snap-fit coupling. The snap-fit coupling also allows easy loading and re-loading by providing for manual plunging of the syringe as shown in FIG. 2. Using a plunger extension that couples to the miniaturized plunger, the same snap coupling as the motor allows easy swapping. Another depiction of assembly together is shown in FIG. 5, including the stepper motor, threaded shaft, with snap-fit coupling to syringe.

Example 3

Assembly and Twin Extruder Design

Figure 6A:
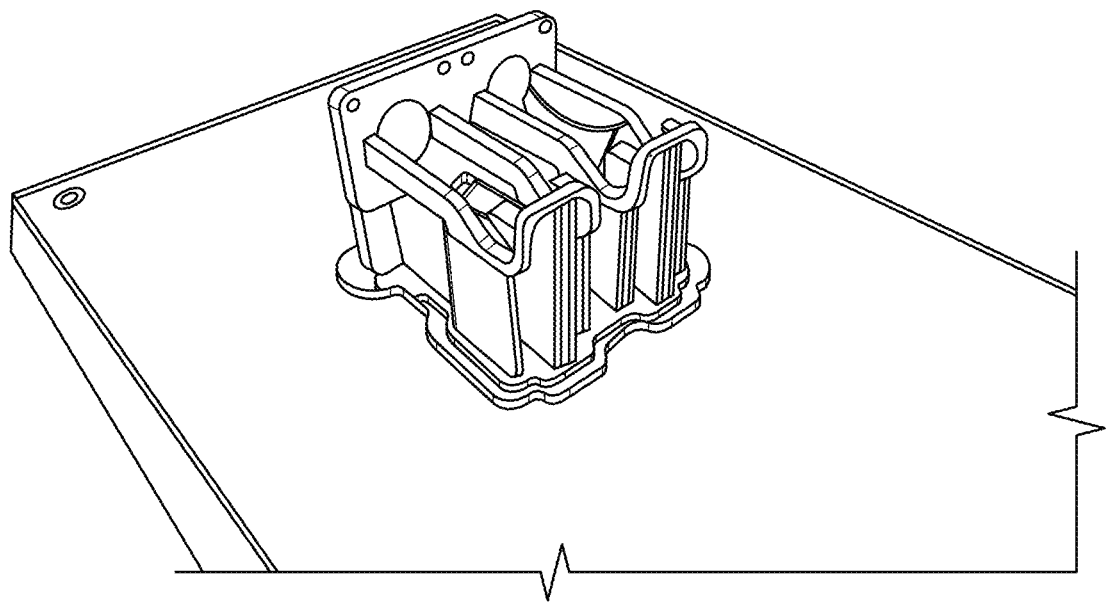
FIG. 6. Depiction of twin extruder. An advantage of the system is that the simplified construction allows for multiple extruders to be assembled together, as shown in (A). In another perspective, the extruder is mounted on the assembly (B).
Figure 6B:
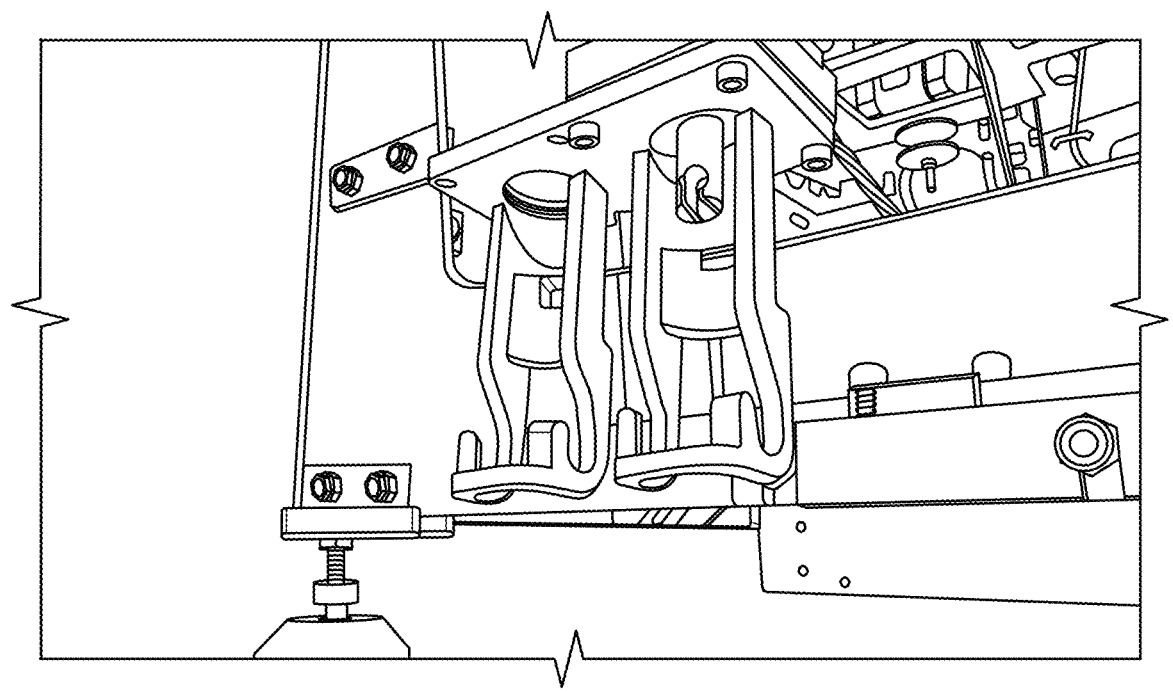

An advantage of the system is that the simplified construction allows for multiple extruders to be assembled together, as shown in FIG. 6. In another perspective, the extruder is mounted on the assembly. In these designs, one could load two different bioink cell types in each extruder, or a cell type and other mechanical substrate in each extruder, with sequential or parallel fabrication, obviating the need to change bioinks/mechanical substrates, as is needed in conventional systems.

Example 4

Bioinks

Figure 4:
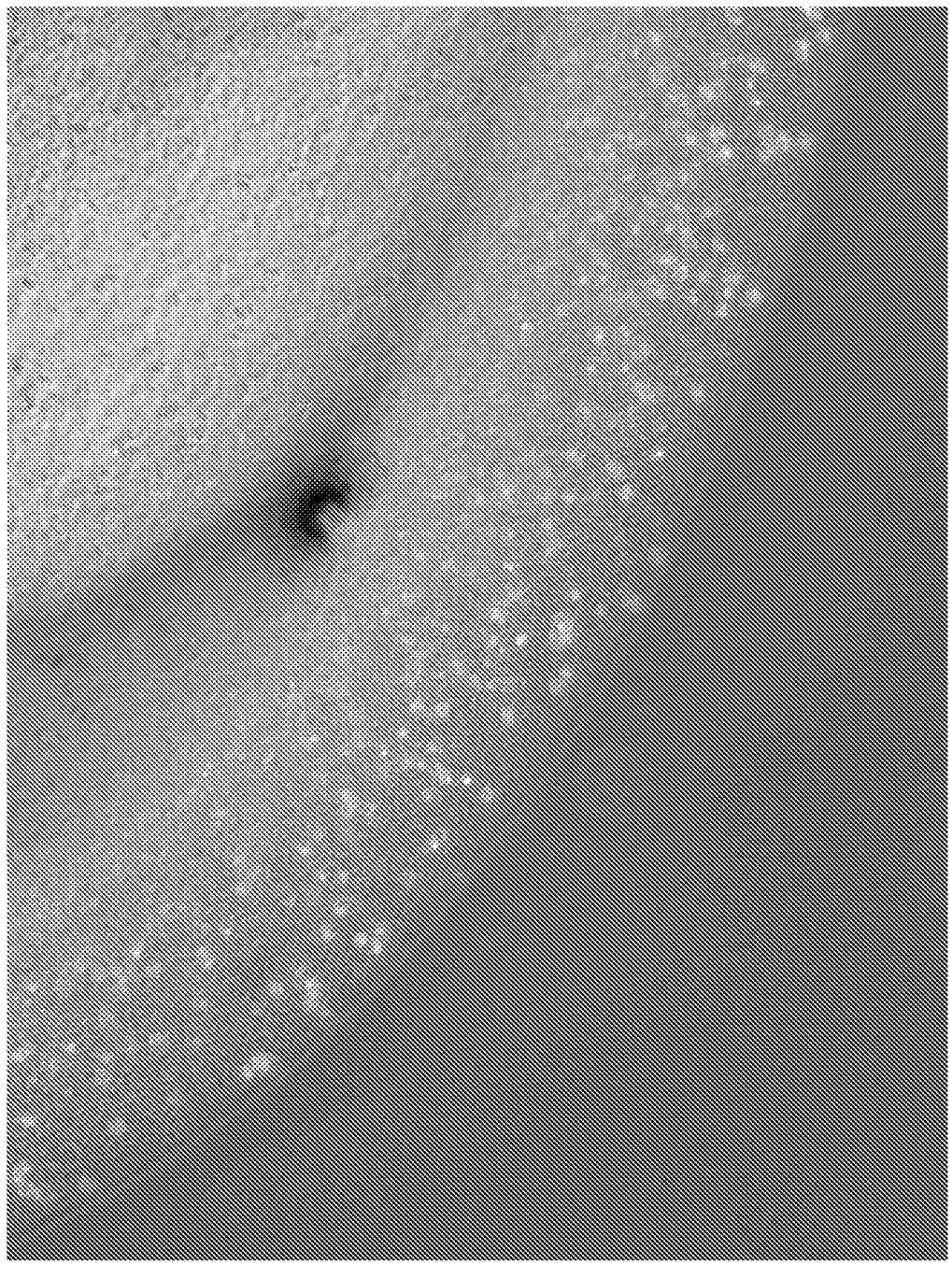
FIG. 4. Stem cell-containing bioink at 4× magnification.

Bioinks are printable materials that can be extruded from a nozzle as liquids, but then stiffened sufficiently to support the weight of successive layers on top of them. We tested a bioink containing cell culture medium, gelatin, and fibrinogen. At 37° C., this ink can be pipetted to suspend cells and fill a syringe. At room temperature it gels, allowing it to be built upon. Silicone can be printed to form scaffolds and microfluidic devices. Exemplary results and views are shown in FIGS. 3 and 4.

Example 5

Preliminary Results

The printer and ink achieved excellent detail, which has continued to improve as settings are optimized (A). An initial printed construct two days after printing (B) and 6 days after printing (C) retained shape. A taller print immediately after printing (D) and after three days (E) also showed excellent cell survival. Printed nuclear GFP stem cells under fluorescence, 3 days post printing (F) were visible inside of the 3 mm tall structure. Exemplary results and views are shown in FIG. 7.

Example 6

Printing Vasculature

Very small and intricate vessel patterns are reportedly among the most difficult to fabricate, but are of high interest as needed for faithfully modeling living systems. The aforementioned bioprinter can support physical design organization of vasculature with superior fabrication results of bioprinted constructions owing to its unique design. In another example, the Inventors use induced pluripotent stem cell brain microvascular endothelial cells (iPSC-BMECs) as superior to human umblinical vein endothelial cells (HU-VECs), with iPSCs-BMECs based on barrier function, enhanced electrical resistance, ability to be cryopreserved, among others. This confers specific advantages when using cells as a consumable for bioprint constructions. Such advantages include consistent cell source between bioprinted constructions and reliable availability.

Example 7

Exemplary Bioprinting Method

This protocol describes the basic process of printing a first-generation vascularized system. Major steps include:
1. Loading bioinks
2. Printer setup
3. Printing
4. Matrix casting
5. Connecting flow
6. Maintenance 0. Checklist
1. Inks
   a. Dissolve and filter fibrinogen.
      See ink preparation protocol for details.
   b. Load Pluronic F-127 into the appropriate syringe
      i. Typically, 3 mL is sufficient for several tests and prints.
      ii. Prepare an additional syringe of Pluronic for post-print adjustment
   c. Chill PBS
      Place in the freezer of Grandmama ~3 hrs prior to use.
   d. Begin thawing Thrombin, Transglutaminase, and possibly acutase and FBS.
2. Hardware, autoclaved, are shown in Table 1.

TABLE 1

| Sterile components |
| --- |
| Gelatin, 15% |
| Dispensing Needles (18 G) |
| Female-Female Luerlock adapters for loading Pluronic syringe |
| PDMS Gaskets |
| Housing lid, capped and wrapped in foil |
| Flow tube, inlet: |
| Female cap |
| Male-male connector |
| Blunt needle |
| Silicone tube, 12 cm |
| Blunt needle, capped |
| Flow tube, outlet: |
| Female cap |
| Male-male connector |
| Blunt needle |
| Silicone tube, 32 cm with tube stops |
| Blunt needle, capped |
| 50 mL Reservoir bottles, 2x |
| Septum caps |
| Septa |

Figure 8:
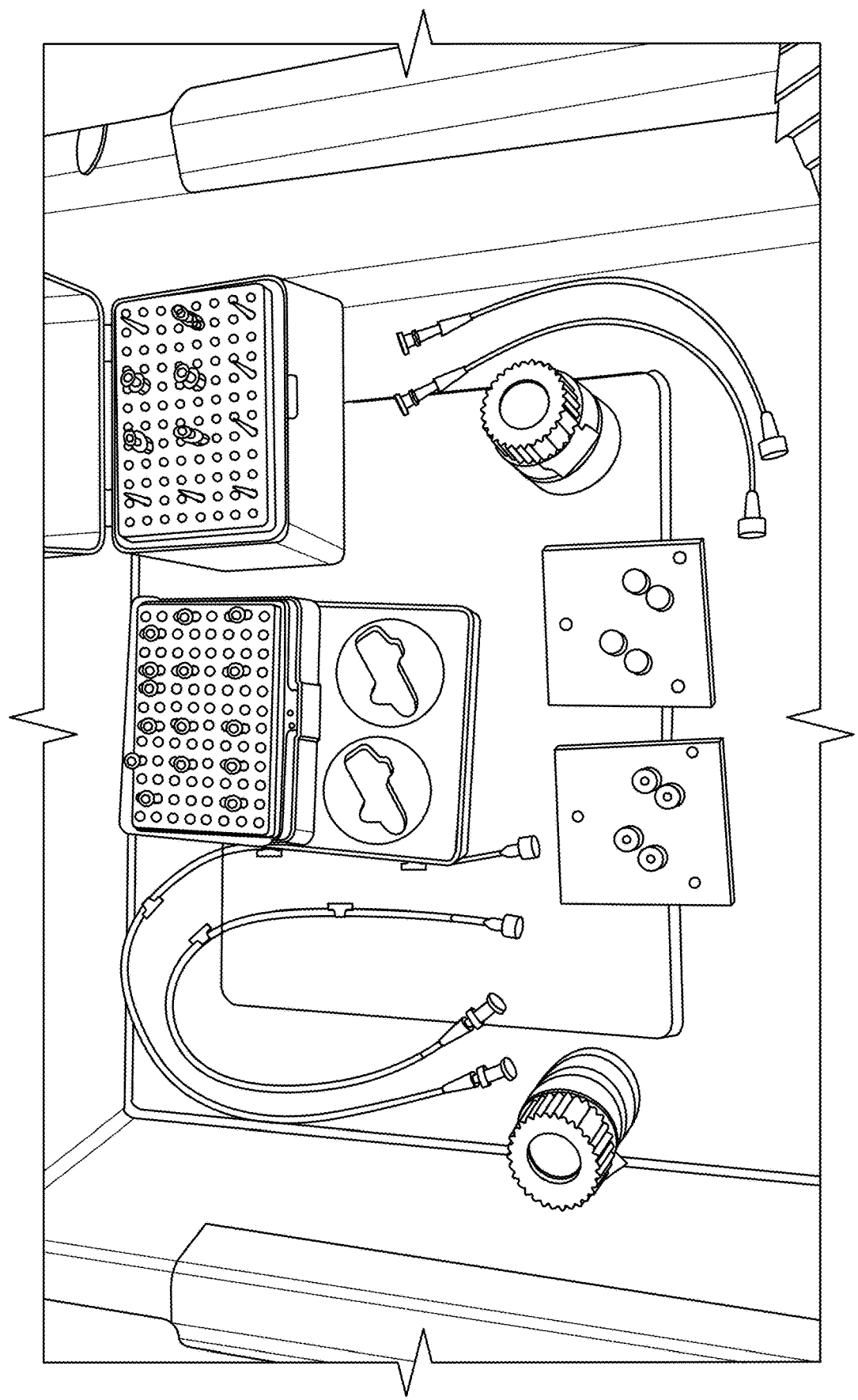
FIG. 8. Depiction of items used in the process.

FIG. 8 depicts items used in the process.
3. Hardware, not autoclaved, as shown in Table 2.

TABLE 2

| Other components |
| --- |
| 60 mm dish |
| Housing base, with retaining ring and M4 bolts |
| 3x M4 wing nuts |
| 4" 16 G reservoir flow needles, 2x |
| 26G x 5/8 venting needles, 2x |
| 0.2 um filters |
| 10 mL syringe |
| Pluronic-filled syringe |

Figure 9:
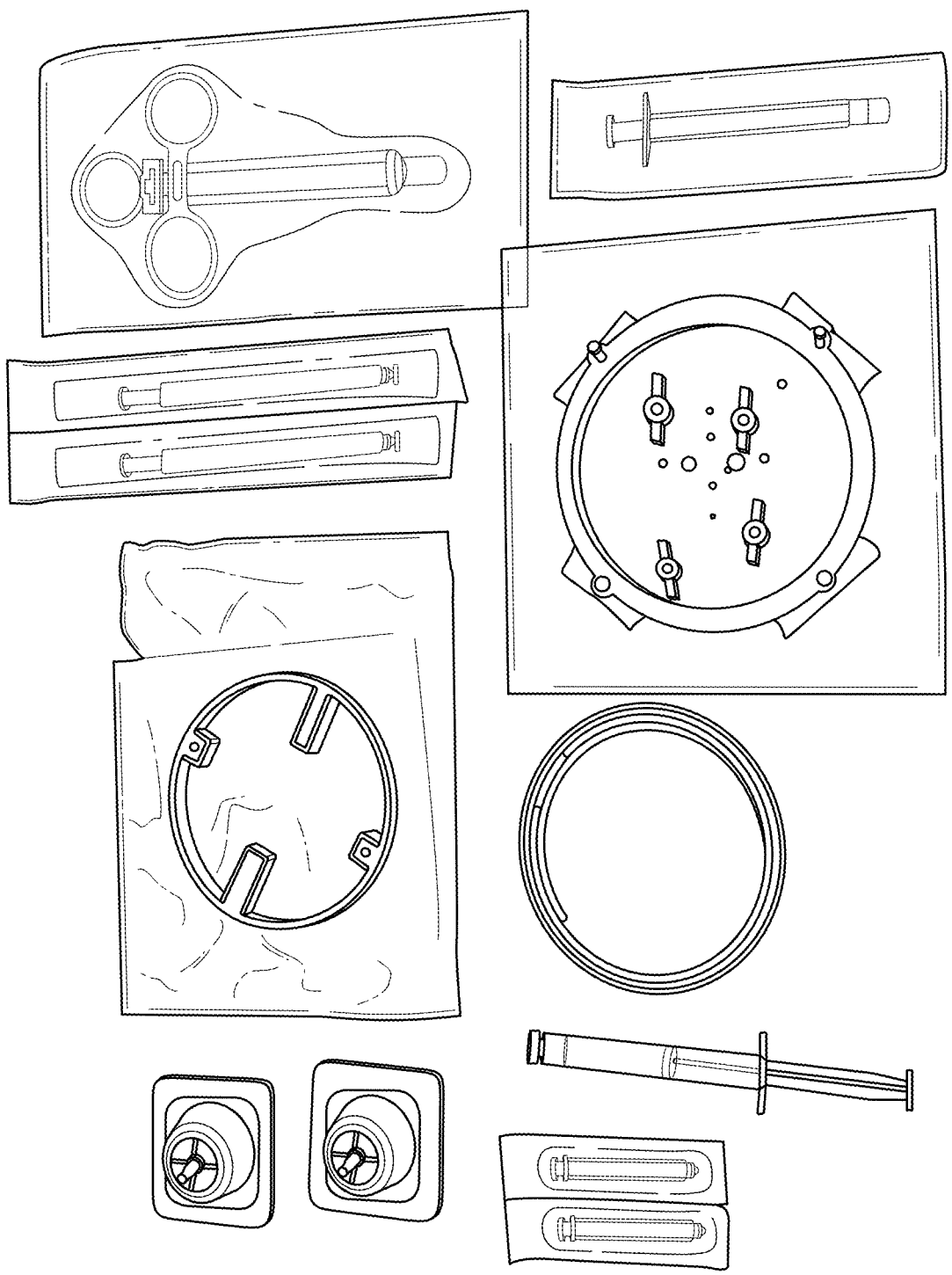
FIG. 9. Depiction of items used in the process.

FIG. 9 depicts items used in the process.

4. Reagents are shown in Table 3.

TABLE 3

Bioprinting reagents

Gelatin (autoclave)
Fibrinogen
Transglutaminase
CaCl2 solution
Thrombin, 100 U/mL
Accutase, 8 mL for two 100 mm dishes
Chilled PBS
mTeSR, 20 mL
PSA 1.a. Autoclave Hardware and Gelatin
 1. Cap lid ports and wrap in aluminum foil.
 2. Prepare inlet and outlet flow tubes and place in an autoclavable box.
 3. Rinse a gasket and place it in an autoclavable box, along with a syringe shaft with coupler
 4. Load a pipet tip box with several 18 G dispensing needles, caps, and female-female Luer lock adapters.
1.b. Dissolve Fibrinogen
 1. Weight out 100 mg of fibrinogen and add to a 50 mL conical tube.
    Attempt to break large pieces apart if possible to improve dissolution. Fibrinogen is kept in Pugsly, Bin_03. Use a 50 mL conical tube to enable filtration with a steriflip tube later.
 2. Add 4.5 mL of DMEM (or the appropriate base medium).
 3. Add 100 µL of PSA.
 4. Add 100 µL of 250 mM $CaCl_2$)
 5. Vortex and incubate for 30 minutes at 37° C.
    Don't push the tube to the bottom of the bead bath: it may overheat.
 6. Attach a steriflip filter and degas for several minutes to reduce bubbles.
 7. Remove vacuum and gently invert the steriflip tube, then restore vacuum to filter.
2. Add Gelatin to Fibrinogen
 1. Add 5 mL of autoclaved 15% gelatin to the dissolved and filtered fibrinogen.
 2. Mix and incubate another 30 mL at 37° C.
 3. 30 minutes before use, add 600 µL of 50 mg/mL transglutaminase.
3. Load Pluronic F-127 into Print Syringes
 1. In the hood, draw out the plunger from a 5 mL syringe and transfer the rubber cap to a printed printer plunger. Sterilize with ethanol.
 2. Attach a plunger adapter to the printer plunger and fully insert the plunger.
 3. Uncap a chilled storage syringe of 30% Pluronic F-127 and add a sterile female-female Luer lock
    adapter. Press the plunger to fill the adapter before coupling the empty 5 mL syringe.
 4. Gently fill the empty syringe vertically, with the empty syringe on top, so that any bubbles rise
    towards the plunger and away from the nozzle.
 5. Fill a 1 mL syringe for post-print adjustment, then cap all syringes. Return the storage syringe to the refrigerator and place the 5 mL print syringe in the printer to acclimate to room temperature.
   The pluronic F-127 will gel quickly inside of the tube. This is fine: it does not need to be liquid to print.
3.b. Load Bioinks—BIO X
Pluronic-127
 1. In a hood, connect a loading syringe full of pluronic F-127 to a CELLINK print syringe.
 2. UNCAP THE BACK OF THE PRINT SYRINGE
 3. Gently load the print syringe vertically, so that any bubbles rise away from the nozzle and recap both syringes.
 4. Print Sacrificial Scaffold
  1. Turn on printer and computer.
  2. Open the Repetier Host print server and press "Connect" if the printer doesn't automatically connect.
  3. Load a .gcode file prepared in Cura.
  4. Home the printer and set a dish on the stage. If a 5 mL syringe hasn't been loaded, load it now.
  5. Press button "1" to move the printhead into position 1.
  6. Uncap the syringe and attach an 18 G plastic syringe. 18 G has been the standard channel size, but can be modified in Fusion 360 through geometric
     dimensions or in Cura through flow. Both plastic and metal nozzles have been used successfully,
     however plastic has become the standard through practice.
  7. Press button "2" to extrude 0.5 mm. Repeat until extrudate emerges.
  8. Pass a small kimwipe below the nozzle to catch and remove the hanging extrudate.
     Extrudate will continue to slowly emerge for several seconds after the motor command is issued. Remove the extrudate after it has stopped emerging in order to leave minimal extra extrudate hanging from the nozzle.
  9. Adjust the bed-nozzle distance with the Z-control buttons until the nozzle is just barely touching the plastic dish.
   Improper starting distance is the primary cause of print failures.
5. Prep Cells
 1. Accutase or trypsinize cells and dilute in a 50 mL syringe
 2. Count the cells and spin down gently.
 3. Aspirate the supernatant and gently resuspend cells in bioink using a 50 mL serological pipet. Approximately 5 mL is appropriate for a gen. 3 perfusion system.
 4. Maintain cell-impregnated ink at 37° C until ready to cast. Attempt to use as soon as possible.
Lewis Bioink/Atala Bioink/Gelatin Dummy Ink
 1. In a hood, open a 5 mL syringe and remove the plunger.
 2. Replace the original plunger with a sterilized coupler plunger.
    Make sure to use the plunger sized for your purposes. A standard 4 mL plunger is recommended for the standard 4 mL construct print.
 3. Attach a sterilized 18 gauge plastic needle tip.
 4. Insert the plastic needle into the bioink solution and draw until the back of the coupling reaches its appropriate starting position. Avoid entraining bubbles.
3.a. Printer Setup—SL-Vertex Bioprinter
 1. Open MatterControl
  a. The printer should connect automatically. If not, see Appendix A: troubleshooting 2. Load an STL or gcode file into the queue
   a. If it is an STL, select "Edit" to center it on the print bed. Printing gcode is recommended, as gcode files can be prepared in Cura, a more feature-rich application.
3. Home all axes by navigating to "Control" and selecting "Home all Axes"
4. Move the print head to the center of the bed by selecting 100 as the move distance and moving it down and to the left.
5. Load inks by manually turning the threaded motor shafts until the bottom of the coupler is just above the top of the syringe slot, with its opening facing outward. The syringe should slot into the syringe slot. The plunger-end coupler should interface with the motor-end coupler without resistance.

3.b. Printer Setup—BIO X
1. Prepare the print file as an STL or gcode
2. Insert a USB drive containing the print files and select "Bioprint"

Current Successful Settings
File: Week 28/Vasculature 5 arcs 0.6 mm.stl
Pressure: 90 kPa
Speed: 10 mm/s
Diameter: 0.95 mm
Layer Height: 0.7 mm
First Layer: 0.7 mm (needs Z-hop)

4. Casting
1. Immediately after printing, cover the print by replacing the dish lid
2. Move the dish into the hood.
3. Add an appropriate amount of pluronic to the ports of the lid on the interior face and gently seat the lid.
4. Screw the wingnuts onto the screws without tightening.
5. Uncap both fill ports and attach a female-female Luer lock adapter to one.
6. Spin down cells in a 50 mL conical tube
7. Aspirate the supernatant and add 5 mL of warm GFT bioink.
8. Add 150 µL of 100 U/mL Thrombin on top of bioink.
9. Using a 25 mL serological pipet, triturate the bioink, cells, and thrombin until well mixed. Working time varies, particularly based on the storage time of the Thrombin.
   This concentration should easily allow at least 10 seconds of working time without noticeable effect. Approximately 30 seconds of working time is expectable before crosslinking begins to become observable, and another minute before cross linking fully inhibits pipetting.
10. Dispense cell-laden ink into the Luer lock adapter, tilting the plate slightly to encourage the ink to spread to the far sides of the pluronic vascular towers.
11. Once the housing is nearly full, dispense the remaining cell laden ink into a 60 mm dish.
12. Remove the female-female adapter and cap this port.
13. Gently tighten the screws to compress the housing. This will compact the headspace and force some bioink out of the remaining uncapped fill port. Wipe this away and cap the uncapped fill port.
14. Transfer the housing and the dish with excess cell ink into the refrigerator and start a timer for 20 minutes.

Printing
1. Fill a syringe with 30% Pluronic F-127
2. Load the syringe into the first extruder
3. Run a test print
4. Place the gasket in the shallow dish lid using the gasket placing tool.
5. Add warm agar
6. Set the dish aside Collection
1. Label appropriate tubes
2. Prepare an appropriate volume of paraformaldehyde (1.75 mL of 32% in 12.25 mL PBS)
3. Shut off the pump.
4. Release the tube restraint.
5. Move the housing and both reservoirs out of the incubator and onto a bench top.
6. Disengage the Luer lock fittings connected to the perfusion housing.
7. Unscrew the wing nuts to release the lid.
8. Transfer the construct into the slicing jig.
9. Section the construct. Using a spatula, transfer the sections into a dish for fixation.
10. Rinse once with PBS, then cover in 4% paraformaldehyde for 20 minutes.
11. While fixing, disassemble reservoirs and flow lines:
    a. Fill a 5 mL syringe with DI water
    b. Remove and discard needles and filters
    c. Examine septa. If reusable, rinse and dry. Otherwise, discard.
    d. Flush silicone tubing with DI water and dry.
12. Aspirate the PFA and rinse in PBS three times.
13. Using a spatula, transfer sections into labeled tubes.

Appendix I
Printer Setup
1. Open MatterController and select your model.
2. Click "Edit". The printer will suggest centering your model. Accept, then save.
3. If necessary, adjust dimensions and save.
4. Connect the printer if it is not already connected
5. Set the feed rate with the command M92 E3000
6. Home the printer.
7. Manually set the Z home.
8. Load a syringe of pluronic F-127 in the appropriate extruder. The left default is extruder 1, which is the default extruder.
9. Purge the nozzle slightly by twisting the drive screw until pluronic F-127 comes out.

Print Settings
General settings for printing are shown in Table 4.

TABLE 4

Print settings

| Setting | Values, Explanations |
|---------|----------------------|
| LAYERS | |
| Nozzle size | 0.7 for pink needle; 0.9 for light green needle Nozzle size is used to calculate the distance to extrude a given volume and the lateral placement of adjacent extrusion lines. Set based on needle ID. |

TABLE 4-continued

Print settings

| Setting | Values, Explanations |
| --- | --- |
| Layer height | 0.7 for pink needle<br>Layer height determines the vertical offset between layers. If too low, the nozzle will attempt to print inside the print as the construct grows faster than the programmed layers. If too high, the nozzle will gradually get farther and farther from the print. Set to the same as nozzle diameter, then decrease slightly if necessary. |
| Perimeters | 10 mm<br>The entire print should be perimeters to avoid infill patterns. |
| Avoid Perimeters | No<br>I'm not sure how this setting affects printing, but tech support once said it can have unintended consequences, so I haven't changed it since. |
| External First | ?<br>So far, this has not presented a clear influence on outcomes. |
| Overlap ends | Yes<br>Full continuity is important in channels, so overlapping is encouraged |
| Merge Overlapping | Yes<br>Gaps are bad, so any overlapping setting is assumed to be good. |
| Expand Thin Walls | Yes<br>If not selected, thin walls may be rounded down, out of existence, creating breaks. |
| INFILL | (N/A) |
| SPEED | |
| Speed, Infill | N/A-Vascular models are not intended to contain infill, only perimeters |
| Speed, Perimeter | 8 mm/s<br>If the speed is too slow, friction will resist extrusion, causing under extrusion. If the speed is too high, the movement will outpace the extrusion, causing breaking and dyssynchronization of the extrusion and movement. |
| Speed, Travel | 15 mm/s<br>If too fast, it can agitate fragile structures when leaving or arriving them. If too slow, travel can allow stringing between islands. |
| SKIRT & RAFT | (N/A) |
| SUPPORT | (N/A) |
| OUTPUT | (N/A) |
| MULT. EXTRUDERS | (N/A) |
| Retraction | If retraction is too low, gel will continue to extrude after the end of moves, forming blobs and strings. If retraction is too high, extrusion will lag behind the beginning of new print moves. |

Filament Settings are shown in Table 4a.

TABLE 4a

Filament Settings

| Setting | Values, Explanations |
| --- | --- |
| LAYERS | |
| Diameter | 0.7 for pink needle;<br>0.9 for light green needle<br>Nozzle size is used to calculate the distance to extrude a given volume and the lateral placement of adjacent extrusion lines. Set based on needle ID. |
| Temp | 0.7 for pink needle<br>Layer height determines the vertical offset between layers. If too low, the nozzle will attempt to print inside the print as the construct grows faster than the programmed layers. If too high, the nozzle will gradually get farther and farther from the print. Set to the same as nozzle diameter, then decrease slightly if necessary. |
| RETRACTION | |
| Length on move | 0.1 mm |
| Extra length on Restart | 0.05 |
| Time for extra Length | 5 s |
| Speed | 65 mm/s |
| Z-lift | 5 mm |

TABLE 4a-continued

| Filament Settings | |
|---|---|
| Setting | Values, Explanations |
| Minimum travel requiring retraction | 3 mm |
| Retract when Changing islands | Yes |
| Min. extrusion Requiring retract. | 0.001 mm |
| Wipe before Retract | No |
| Length on tool Change | 0 |
| Extra on tool Change | 0 |
| EXTRUSION | |
| Extrusion multiplier | 0.6 x  The extrusion multiplier manually scales the extrusion up or down. At its default (1), the flow will be too high, unless the nozzle diameter is decreased. This can work, but will mean that adjacent lines are marginally further apart. |
| Width | 100%; 100%; 0% |

Designing the Construct

Construct design begins with a concept and then proceeds through a series of refinement steps. The standard construct used in this design was started with the decision to have two towers connect to ports on a lid, and to connect those towers by several lateral channels. An initial construct based on these principles was modeled, and then a gasket was designed around the construct.

Following the design of the first draft of a construct, a mold of the gasket was printed in PLA and used to cast PDMS. The production of a working gasket and enclosure prompted later construct designs to fit key dimensions to these reusable parts. Key dimensions are the distances between the tower and the width of the gasket. The number of channels, the width of the channels, the shape of the channels, and the diameter of the towers were adjusted iteratively.

Channel width: The channel width must be compatible with the nozzle diameter specified in the slicer. If channels are thinner, the slicer will not lay a path along them. If channels are too wide, the slicer will lay down multiple lines along each channel. To set the right channel width, select a nozzle size; optimize print settings for this nozzle size; then used the resulting optimal nozzle size parameter to define the width of channels in CAD.

Channel number: Greater channel numbers increases the bulk flow through the construct until the tower diameter is more constricting than the channels. Based on slicing habits, though, excessive more channels may increase the possibility of dead channels: those that don't effectively connect along a continuous path from inlet to outlet.

Channel shape: Arcing channels were selected because angled channels with straight lines were prone to distortion and dragging as the printhead moved.

Hardware Guide

Dispensing Needles

Typically green plastic 18 G dispensing needles (autoclaved). These have an outlet ~1 mm in diameter. Slicing profiles for the SL Vertex usually assume _____0.8 mm diameter, with a flow of 1.2 or 1 mm with a flow of 1. When printing on the BIO X, the nozzle diameter is set for _____0.8 mm with a pressure of or 1 mm with a pressure of _____.

23 G—0.432 mm (432 um) Orange tip
  20 G—0.660 mm (660 um) Pink tip
  18 G—0.965 mm (965 um) Green tip Example 8

Staining and Imaging Bioprinted Constructs

Solutions

Live/Dead Stain

50 μL of 1 mM stock Calcein in DMSO—Dilute 50 ug Calcein in 50 uL DMSO
  2 mL of 4 uM Ethidium Homodimer/2 uM Calcein—To 2 mL of PBS, add:
    4 μL of 2 mM Ethidium Homodimer
    4 μL of 1 mM Calcein
  2 mL of 5 uM Propidium Iodide+2 uM Calcein—To 2 mL of PBS, add:
    6.6 uL of 1 mg/mL Propidium Iodide
    4 μL of 1 mM Calcein 4% Paraformaldehyde
  12.25 mL PBS+1.25 mL 32% Paraformaldehyde Blocking & Permeabilization Buffer
  2 mL/section. 10 mL recommended.
  9 mL PBS
  1 mL Donkey Serum
  15 uL Triton X Wash Buffer 100 uL TWEEN in 100 mL PBS Hoescht Stain 33342 (w/2ndary Abs)

2 uL Hoescht in 5 mL PBS

Common Primary Antibodies:

iPSCs can be characterized using surface antigen antibodies listed in Table 5.

TABLE 5 iPSC characterization antibodies

|  | Mouse anti Hs | Rabbit anti Hs |
|---|---|---|
| 1 mL blocking/ perm buffer | 4 uL Tra 181 | 4 uL SOX2 |
|  | 4 uL Tra 1 60 | 4 uL Nanog |
|  | 4 uL SSEA4 | 4 uL OCT4 |

Induced motor neurons (iMiNs) can be characterized using surface antigen antibodies listed in Table 6.

TABLE 6

Induced motor neuron (iMN) characterization antibodies

|  | Mouse anti Hs | Rabbit anti Hs |
|---|---|---|
| 1 mL blocking/ perm buffer | 4 uL SMI32, Biolegend (Cyto) | 4 uL Tuj1/TUBB3, Abnova (Cyto) |
|  | 10 uL Olig2, Millipore (Nuclear) | 4 uL Tuj1/TUBB3, Abnova (Cyto) |
|  | Beta Actin |  |
|  | FITC-Dextran |  |
|  | FITC-HAS |  |
|  | Insulin-FITC |  |

Other cell types (such as HEK293T) can be characterized using surface antigen antibodies listed in Table 7.

TABLE 7

Antibodies for characterizing other cell types

|  | Mouse anti Hs | Rabbit anti Hs |
|---|---|---|
| 1 mL blocking/ perm buffer | 4 uL Tra 181 | 4 uL SOX2 |
|  | 4 uL Tra 1 60 | 4 uL Nanog |
|  | 4 uL SSEA4 | 4 uL OCT4 |

Secondary Ab stains for the aforementioned antibodies are listed in Table 8.

TABLE 8

Secondary antibodies

|  | Anti Mouse | Anti Rabbit |
|---|---|---|
| 4 mL Blocking buffer | 16 uL Alexa 647, anti-Ms | 16 uL Alexa 568, anti-Rb |

Staining

| Wave length | Name | Target | Section A | Section B | Section C |
|---|---|---|---|---|---|
| 405 (Blue) | DAPI | DNA |  |  |  |
| 488 (Green) | GFP | Nuclear? |  |  |  |
| 568 (Orange) | Cy3/TritC | Ms 1° Ab | SSEA4 | Tra 1 81 | Tra 1 60 |
| 647 (Red) | Cy5 | Rb 1° Ab | OCT4 | SOX2 | Nanog |

Sectioning

Section the construct using a sectioning jig. Transfer the slices into a 60 mm dish or 6-well plate and rinse in PBS.

Viability Staining

1. Incubate sectioned constructs in Live/Dead staining dyes for 30 minutes at RT
2. Rinse three times in PBS
3. Image. Including excitation and emission values are listed in Table 9.

TABLE 9

Visualization

| Dye | Excitation max | Excitation Filter | Emission Max | Emission Filter | Comparable Dyes |
|---|---|---|---|---|---|
| Calcein AM | 488 nm | 485/20 | 520 nm | 530/25 | FITC, EGFP |
| Ethidium Homodimer | 528 nm |  | 617 nm |  | RFP, TRITC, Texas Red |
| Propidium Iodide | 535 nm |  | 617 |  | RFP, TRITC, Texas Red |

* Propidium iodide, EthD-1, and scaffold samples in Bin 1 Pugsly, calcein in Fester Fixing Initial fixation was performed overnight, but later fixations have been incubated for 30 minutes to avoid over-crosslinking and reducing permeability. Rinse 3× and store in PBS. HUVECs on Fibrin: HUVECs on fibrin are fixed for 20 minutes Staining, IHC 1) Block and Permeabilize
    Submerge sections in blocking & permeabilization buffer overnight at 4° C.
    HUVECs on Fibrin: HUVECs are blocked for 1 hr prior to primary stain.
2) Rinse once with PBS.
3) Stain with Primary Antibodies
    Incubate overnight at 4° C.

4) Wash three times with PBS+TWEEN

Incubate at room temperature for five minutes between washes.

5) Stain with Secondary Antibodies

Spin down secondaries before preparation.

Incubate for two hours at room temperature, shielded from light.

6) Wash with PBS

7) Stain with Hoescht or DAPI

8) Rinse

Imaging

After staining with Viability stain or antibodies stains, Place the samples on glass slides <?> Current attempts have placed sections in glass slides, which have the advantage of letting gravity firmly set them in place, but the disadvantage of allowing evaporative drying to warp the sample. An attempt to image in a well filled with PBS caused difficulties focusing, but is worth subsequent attempt.

TABLE 10

Visualization

| Dye | Excitation max | Excitation Filter | Emission Max | Emission Filter | Comparable Dyes |
|---|---|---|---|---|---|
| GFP | 488 nm | 485/20 | 520 nm | 530/25 | FITC, EGFP |
| Alexa Fluor 568 (Typically Rb) | 578 nm | 568 | 603 nm | | Texas Red |
| Alexa Fluor 647 (Typically Ms) | 650 nm | 594/633 | 665 nm | | Cy5 |

Example 9

This protocol describes the preparation of several bioinks.

Reagents

TABLE 11

Firbrinogen-Gelatin (F-G) Bioink

| Reagent | Cat. # | Location | [Stock] | [Final] | 10 mL | 25 mL |
|---|---|---|---|---|---|---|
| mTeSR Medium | | 4° C., Gomez | 1x | — | — | — |
| Gelatin | Sigma G2500-100G | Chemical Shelf | Powder | 35 mg/mL | 350 mg | 875 mg |
| Fibrinogen | Sigma 341573-1GM | 4° C., Fester; Chemicals | Powder | 20 mg/mL | 200 mg | 500 mg |
| Hyaluronic Acid | Sigma 53747-1G | 4° C., Fester; Chemicals | Powder | 3 mg/mL | 30 mg | 75 mg |
| PSA | | 4° C., Fester; PSA | 100x | 1x | 100 μL | 250 μL |
| Glycerol (optional) | | | 1x | 10% | 1000 μL | 2500 μL |
| Collagen (optional) | | | 1x | 10% | 1000 μL | 2500 μL |

TABLE 12

Firbrinogen-Gelatin-Thrombin (F-G-T) Bioink

| Reagent | Cat. # | Location | [Stock] | [Final] | 10 mL | 25 mL |
|---|---|---|---|---|---|---|
| PBS | | 4° C., Gomez | 1x | — | — | — |
| Gelatin | Sigma G2500-100G | Chemical Shelf | 150 mg/mL | 75 mg/mL | 5 mL | 12.5 mL |
| Fibrinogen | Sigma 341573-1GM | 4° C., Fester; Chemicals | 50 mg/mL | 10 mg/mL | 2 mL | 5 mL |
| CaCl2 | | Chemical Shelf | 250. mM | 2.5 mM | 100 μL | 250 μL |
| Transglutamase | Mod. Pantry 1203-50 | Fester, bottom | 50 mg/mL | 2 or 10 mg/mL | 0.4/2 mL | 1/5 mL |
| Thrombin | Sigma T4648-10KU | | 100 U/mL | 1 U/mL | 100 μL | 250 μL |
| Glycerol (optional) | | | 1x | 10% | 1000 μL | 2500 μL |
| Collagen (optional) | | | 1x | 10% | 1000 μL | 2500 μL |

TABLE 13

| Pluronic F-127 | | | | | | |
|---|---|---|---|---|---|---|
| Reagent | Location | [Stock] | [Final] | 10 mL | 25 mL |
| PBS | Culture room shelf | 1x | — | — | — |
| Pluronic F-127 Sigma P2443-250G | Chemical Shelf | Powder | 300 mg/mL | 3 g | 7.5 g |
| PSA | 4° C., Grandmama, door −20° C., Fester, conical drawers | 100x | 1x | 100 μL | 250 μL |
| Glycerol (optional) | Chemical Shelf | 1x | 10% | 1 mL | 2.5 mL |

Fibrinogen-Gelatin-Thrombin (F-G-T) Bioink (Lewis Composition)
15% Gelatin Solution (15 mL for 25 mL of Lewis Bioink)
1. Measure out 15 mL of PBS and heat it to 70° C.
2. Weigh out 2.25 g of gelatin
3. Combine the gelatin with 12 mL of hot PBS and place in a shaking incubator.
4. Dilute to 15 mL after gelatin is dissolved.
   a. A shake-ball can be added to improve mixing if desired 50 mg/mL Fibrinogen Solution (2 mL for 10 mL of Lewis Bioink)
1. Weigh out 100 mg of fibrinogen.
2. Dissolve in 1.5 mL of PBS (w/o Mg+Ca). Bring up to 2 mL.
3. Gently shake at 37° C. for at least 45 minutes.

50 mg/mL Transglutamase Stock Solution:
1. Weigh out 250 mg of Transglutamase
2. Add the TG to 4.5 mL of PBS (w/o Ca/Mg) and bring to a final volume of 5 mL
3. Aliquot and freeze. 250 mM $CaCl_2$) stock solution
1. Dissolve 277.5 mg in 10 mL PBS (w/o Ca—Mg)
2.

Preparing F-G-T Bioink (10 mL)
1. To 2.4 mL of warm PBS, add 5 mL of 15% gelatin.
2. Add 100 μL of $CaCl_2$).
3. Add 2 mL of 50 mg/mL Fibrinogen. This brings the volume to 8.5 mL
4. Mix thoroughly by shaking at 37° C. for 30 minutes.
5. When ready to use the solution, add 400 μL of 50 mg/mL Transglutamase. Mix gently.
6. Incubate for 20 minutes around room temperature. Elevate temperature slightly if necessary to avoid allowing bioink to cool and gel.
7. Centrifuge cells and aspirate supernatant.
8. Add the bioink to the centrifuged cells and gently triturate with a serological pipet to resuspend the cells.
9. Add 40 μL of 100 U/mL Thrombin. Triturate 5 times, for approximately than 10 seconds, and deposit into containment housing.

Pluronic F-127 Sacrificial Ink
Preparing 25 mL of 30% Pluronic F-127
1. Prepare 25 mL of 2% PSA in PBS by adding 500 μL of PSA into 24.5 mL of PBS.
2. Chill the PBS+2% PSA solution as much as possible without freezing.
3. Weigh out 7.5 g of Pluronic F-127.
4. In a 50 mL conical, alternate between adding pluronic F-127 and PBS. Leave space to adjust volume upward to final volume.
5. Mix thoroughly by vortexing.
6. Place in a rotator in the cold room overnight at a low speed.

Preparing 10 mL of 30% Pluronic F-127+Glycerol
1. Chill 10 mL of PBS to just above freezing.
2. Autoclave a ball bearing
3. Weigh out 3 g of Pluronic F-127.
4. In a 50 mL conical, alternate between adding pluronic F-127 and PBS. Leave space to adjust volume upward to final volume.
5. Mix thoroughly by vortexing.
6. Place in a rotator in the cold room overnight at a low speed.

Gelatin-Only Test Inks
60% Gelatin Test ink
30% Gelatin Test Ink

Example 10

Perfusion System

Described herein is a perfusion system enclosure. It consists of two polycarbonate plates separated by a silicone gasket with luer lock fittings to allow for fluid to be pumped through the assembly.

TABLE 14a

| Bill of Materials | | | |
|---|---|---|---|
| Part | Quant. | Vendor | Cat. # |
| Polycarbonate sheets, 6x6 in × 1/4 in | 1 | McMaster | 8574K281 |
| Hex bolts | | | |
| Wing Nuts | | | |
| Plastic Quick-Turn Tube Coupling Plugs, 1/4"-28 UNF Male Thread Size, Polycarbonate Female Luer lock caps | 4 | McMaster | 51525K241 |
| Nonwhitening Cement for Acrylic Scigrip 4, 4 oz. Can | 1 | McMaster | 7517A1 |
| Silicone pump tubing | | | |

TABLE 14b

| Printed Tools | | |
|---|---|---|
| Tool | Vendor | Cat. # |
| Drilling template | | |
| Gasket mold | | |

TABLE 14c

| Tools | | |
|---|---|---|
| Tool | Vendor | Cat. # |
| Drill | | |
| 3D printer | | |
| Drill bits: 5/32, 7/32 | | |
| Hole template (and marker) | | |
| Tap-1/4-28 | McMaster | 2521a661 |
| Syringe with 23G needle | | |

Figure 10:
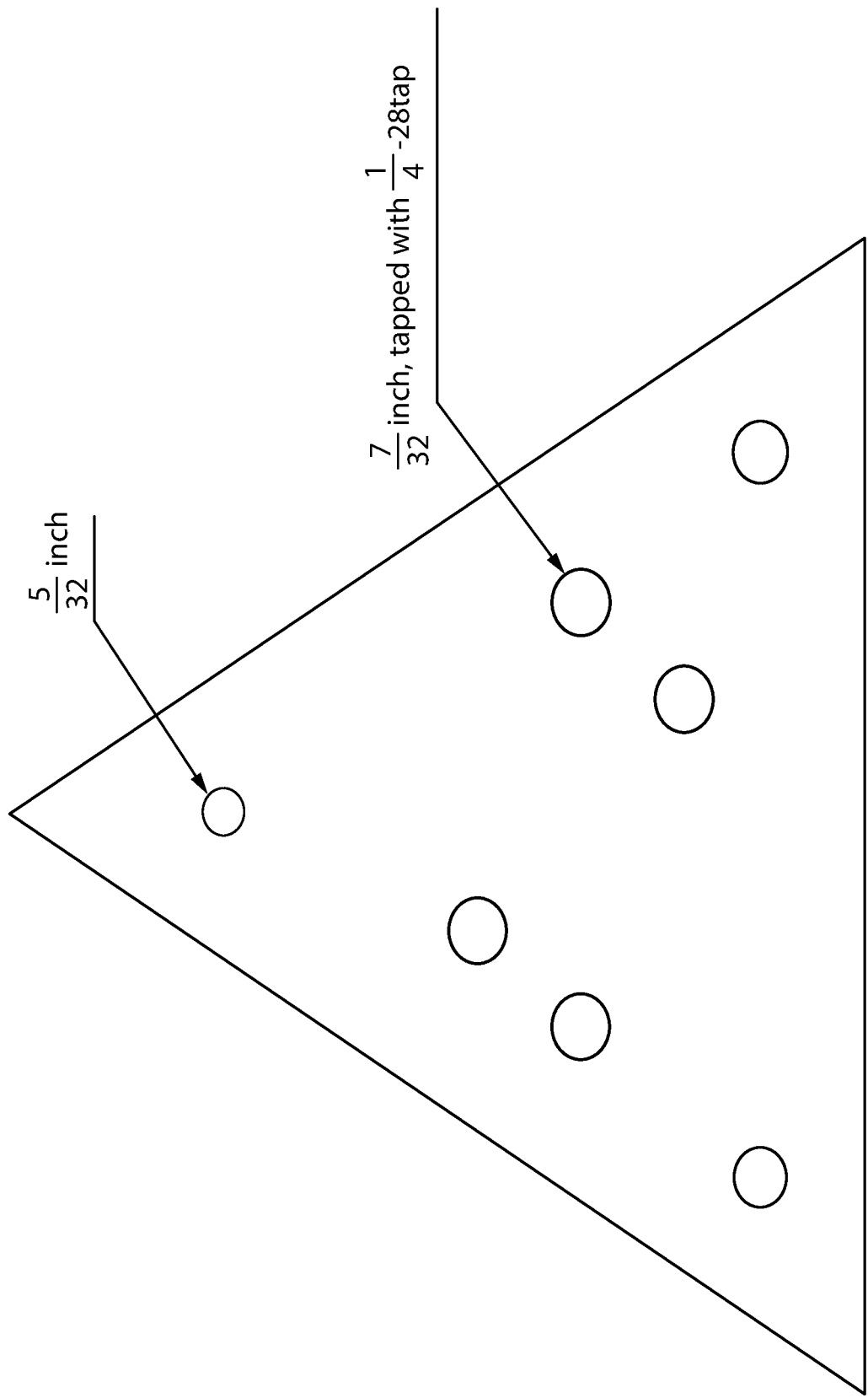
FIG. 10. Depiction of the plate design.

Polycarbonate Plates:
1. Cut ¼" plates to 3"×3"
2. Use the hole template to mark the location of drill holes, then drill.
   a. 5/32" holes for hex bolts
   b. 7/32" holes for tapped holes
3. Tap the four appropriate holes with 14-28 taps.
   a. Tap should extend will through to ensure sufficient tapping.
4. Screw in the threaded Luer lock connectors, then unscrew each 1 full turn
5. Apply acrylic cement to the point where the threaded connectors meet the polycarbonate, then turn to tighten.
   a. Apply the solvent carefully to avoid dripping!
6. Apply a bit more solvent cement to the seam and allow it to evaporate
7. Flip the lid over and apply solvent cement to the interior seam, allowing it to evaporate.
FIG. 10 depicts the plate design.

Spacing Ring:
1. Print the spaceing ring

Gasket
1. Print the gasket molds
2. Mix 18 mL of elastomer base with 2 mL of hardener.
3. Mix thoroughly with a spatula.
   a. Thorough mixing is critical. Beat the solution until bubbles occlude the entire volume. Alternate between stirring, beating, and spinning the spatula to mix on all scales. Pay special attention to the bottom tip of the conical, in which mixing is especially difficult.
4. Degass by applying a vacuum using a steriflip tube.
   a. Degassing will take ~30 minutes.

Casting the PDMS Gasket
1. To a 50 mL conical tube, add 18 mL of Silicone elastomer base
   The silicone elastomer is highly viscous. Use a 50 mL serological pipet and be patient.
2. Add 2 mL of catalyst
3. Mix vigorously for five minutes with a spatula.
   Alternate between twirling a spatula within an immobilized tube, scooping, and mixing. The mixture should be cloudy with bubbles throughout.
4. Degas the mixture thoroughly.
   Attach a steriflip tube to degas. Degassing takes approximately 30 minutes.
5. Pour the silicone solution into the gasket mold The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the compositions and methods related to expansion of stem cells, including bioprinting designs and techniques for printing using bioprinting, bioink constituents, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A bioprinter for dispensing at least one biomaterial, comprising:
 a processor configured to determine a path;
 a support assembly, comprising one or more linear rods; and
 a gantry comprising:
  at least one extruder, each extruder comprising a nozzle and a tube,
  a plunger,
  a threaded shaft, and
  a stepper motor,
 wherein the processor is operatively coupled to the support assembly to move the one or more linear rods along a determined path, and operatively coupled to the stepper motor,
 wherein the one or more linear rods are attached to the gantry,
 wherein the plunger is inside the tube and comprises an attachment member coupled to the threaded shaft,
 wherein the attachment member comprises reciprocating members on each of the plunger and threaded shaft, the reciprocating members including a first reciprocating member coupled to the plunger and a second reciprocating member coupled to the threaded shaft such that the plunger is coupled to the threaded shaft with a snap-Fit coupling between the first reciprocating member and the second reciprocating member,
 wherein the threaded shaft is mechanically coupled to the stepper motor,
 wherein the nozzle is at one end of the tube.

2. The bioprinter of claim 1, wherein the stepper motor is configured to turn the threaded shaft directly.

3. The bioprinter of claim 2, wherein the stepper motor coupled with the threaded shaft is further configured to directly move the plunger of the extruder.

4. The bioprinter of claim 1, wherein the bioprinter comprises two extruders.

5. The bioprinter of claim 1, wherein the plunger is configured to exert pressure through the nozzle.

6. A bioprinted assembly made by the bioprinter of claim 1.

7. The bioprinted assembly of claim 6, comprising a layer of vascular cells in an organized fashion deposited on a substrate.

8. The bioprinted assembly of claim 7, comprising one or more non-vascular cells.

9. The bioprinted assembly of claim 8, wherein the non-vascular cells are derived from induced pluripotent stem cells (iPSCs).

10. The bioprinted assembly of claim 7, comprising induced pluripotent stem cell-derived endothelial cells (iECs).

11. The bioprinter of claim 1, wherein the one or more linear rods includes at least two linear rods that are attached to the gantry.

12. The bioprinter of claim 1, further comprising a plunger extension configured to couple to the plunger for manual plunging when loading and unloading ink.

13. The bioprinter of claim 12, wherein the plunger extension is coupled to the plunger with a snap-fit coupling.

14. A bioink, comprising:
 a quantity of at least one cell type suspended in a substrate suitable for bioprinting, the at least one cell type comprising induced pluripotent stem cell-derived endothelial cells (iECs),
 wherein the substrate comprises cell culture media gelatin and fibrinogen.

15. The bioink of claim 14, wherein at 37° C., the bioink is capable of being pipetted to suspend the iECs and fill a syringe, and at room temperature, the bioink gels, allowing the bioink to be built upon.

16. A bioink, comprising:
 a quantity of at least one cell type suspended in a substrate suitable for bioprinting, the at least one cell type comprising one or more non-vascular cells, wherein the substrate comprises cell culture media gelatin and fibrinogen.

17. The bioink of claim 16, wherein the non-vascular cells are derived from induced pluripotent stem cells (iPSCs).

18. The bioink of claim 16, wherein at 37° C., the bioink is capable of being pipetted to suspend the one or more non-vascular cells and fill a syringe, and at room temperature, the bioink gels, allowing the bioink to be built upon.

* * * * *